United States Patent
Adams et al.

(10) Patent No.: US 9,682,392 B2
(45) Date of Patent: *Jun. 20, 2017

(54) METHOD FOR APPLYING VARYING AMOUNTS OR TYPES OF ADHESIVE ON AN ELASTIC STRAND

(71) Applicant: Nordson Corporation, Westlake, OH (US)

(72) Inventors: Brian K. Adams, Gainesville, GA (US); Michael W. Harris, Shoreview, MN (US); Joel E. Saine, Dahlonega, GA (US)

(73) Assignee: Nordson Corporation, Westlake, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/052,910

(22) Filed: Feb. 25, 2016

(65) Prior Publication Data

US 2016/0166441 A1 Jun. 16, 2016

Related U.S. Application Data

(60) Continuation-in-part of application No. 14/644,318, filed on Mar. 11, 2015, which is a continuation of
(Continued)

(51) Int. Cl.
*B05D 5/10* (2006.01)
*B05B 13/02* (2006.01)
(Continued)

(52) U.S. Cl.
CPC .... *B05B 13/0207* (2013.01); *A61F 13/15593* (2013.01); *A61F 13/49017* (2013.01);
(Continued)

(58) Field of Classification Search
CPC ........................................................ B05D 1/26
See application file for complete search history.

(56) References Cited

U.S. PATENT DOCUMENTS 2,428,284 A 9/1947 Krogel
2,823,518 A 2/1958 Murray
(Continued)

FOREIGN PATENT DOCUMENTS

EP 0096453 A2 12/1983
EP 0097414 A1 1/1984
(Continued)

OTHER PUBLICATIONS

European Patent Office, Supplementary European Search Report in EP Application No. 03721603, Feb. 8, 2007.
(Continued)

*Primary Examiner* — Xiao Zhao
(74) *Attorney, Agent, or Firm* — Baker & Hostetler LLP

(57) ABSTRACT

A method and devices for dispensing adhesive onto an elastic strand are configured to apply first, second, and third volumes of adhesive onto first, second, and third portions of the elastic strand, respectively. When the elastic strand is adhesively secured to a substrate to form a personal disposable hygiene product, the first and third portions of the elastic strand define opposing ends of the elastic strand, which are adhered with a larger amount of adhesive or a stronger adhesive material capable of limiting movement of the strand at the opposing ends. The method and devices advantageously use a module and nozzle which maintain separation between first and second adhesive streams received from different adhesive supplies at least until flow within the nozzle. This arrangement enables use of different
(Continued)

adhesives to form the first, second, and third volumes, as well as "wet-on-wet" contact dispensing using multiple nozzle outlets.

22 Claims, 13 Drawing Sheets

Related U.S. Application Data application No. 14/456,418, filed on Aug. 11, 2014, now Pat. No. 9,067,394, which is a continuation-in-part of application No. 13/444,126, filed on Apr. 11, 2012, now Pat. No. 9,034,425, application No. 15/052,910, which is a continuation-in-part of application No. 14/644,326, filed on Mar. 11, 2015, which is a division of application No. 13/444,126, filed on Apr. 11, 2012, now Pat. No. 9,034,425.

(51) Int. Cl.
    *A61F 13/49*     (2006.01)
    *B05C 5/02*     (2006.01)
    *B05C 9/06*     (2006.01)
    *B32B 37/12*     (2006.01)
    *A61F 13/15*     (2006.01)

(52) U.S. Cl.
    CPC .............. *B05C 5/0241* (2013.01); *B05C 9/06* (2013.01); *B32B 37/1292* (2013.01); *A61F 2013/1591* (2013.01); *B32B 2555/02* (2013.01)

(56) References Cited

U.S. PATENT DOCUMENTS

| | | |
|---|---|---|
| 2,841,020 A | 7/1958 | Van Deventer, IV |
| 3,219,276 A | 11/1965 | Norris |
| 3,640,461 A | 2/1972 | Koll |
| 3,890,926 A | 6/1975 | Teed |
| 3,911,173 A | 10/1975 | Sprague, Jr. |
| 3,997,308 A | 12/1976 | Drummond et al. |
| 4,031,854 A | 6/1977 | Sprague, Jr. |
| 4,048,861 A | 9/1977 | Woidke et al. |
| 4,050,410 A | 9/1977 | Stroszynski |
| 4,135,903 A | 1/1979 | Ohsato et al. |
| 4,185,981 A | 1/1980 | Ohsato et al. |
| 4,222,758 A | 9/1980 | Stotler et al. |
| 4,325,372 A | 4/1982 | Teed |
| 4,488,665 A | 12/1984 | Cocks et al. |
| 4,530,862 A | 7/1985 | Kerzel |
| 4,666,542 A | 5/1987 | De Jonckheere |
| 4,687,477 A | 8/1987 | Suzuki et al. |
| 4,711,683 A | 12/1987 | Merkatoris |
| 4,762,582 A | 8/1988 | de Jonckheere |
| 4,764,234 A | 8/1988 | Smits et al. |
| 4,785,996 A | 11/1988 | Ziecker et al. |
| 4,801,051 A | 1/1989 | Lewis et al. |
| 4,801,345 A | 1/1989 | Dussaud et al. |
| 4,815,660 A | 3/1989 | Boger |
| 4,842,666 A | 6/1989 | Werenicz |
| 4,844,003 A | 7/1989 | Slautterback et al. |
| 4,891,249 A | 1/1990 | McIntyre |
| 4,917,696 A | 4/1990 | De Jonckheere |
| 4,949,668 A | 8/1990 | Heindel et al. |
| 4,995,333 A | 2/1991 | Keller et al. |
| 5,066,428 A | 11/1991 | Manlowe et al. |
| 5,171,512 A | 12/1992 | Mende et al. |
| 5,267,693 A | 12/1993 | Dickey |
| 5,275,676 A | 1/1994 | Rooyakkers et al. |
| 5,277,344 A | 1/1994 | Jenkins |
| 5,322,729 A | 6/1994 | Heeter et al. |
| 5,338,569 A | 8/1994 | Hatch |
| 5,340,648 A | 8/1994 | Rollins et al. |
| 5,342,647 A | 8/1994 | Heindel et al. |
| 5,360,629 A | 11/1994 | Milbourn et al. |
| 5,382,312 A | 1/1995 | Raterman |
| 5,406,782 A | 4/1995 | Inuyama et al. |
| 5,413,654 A | 5/1995 | Igaue et al. |
| 5,418,009 A | 5/1995 | Raterman et al. |
| 5,421,941 A | 6/1995 | Allen et al. |
| 5,429,694 A | 7/1995 | Herrmann |
| 5,501,756 A | 3/1996 | Rollins et al. |
| 5,505,995 A | 4/1996 | Leonard |
| 5,507,909 A | 4/1996 | Rollins et al. |
| 5,525,175 A | 6/1996 | Blenke et al. |
| 5,540,774 A | 7/1996 | Smitherman |
| 5,540,804 A | 7/1996 | Raterman |
| 5,553,758 A | 9/1996 | Melendy et al. |
| 5,576,091 A | 11/1996 | Zajaczkowski et al. |
| 5,582,668 A | 12/1996 | Kling |
| 5,645,220 A | 7/1997 | Hohndorf |
| 5,683,752 A | 11/1997 | Popp et al. |
| 5,688,555 A | 11/1997 | Teng |
| 5,779,799 A | 7/1998 | Davis |
| 5,785,258 A | 7/1998 | Akin et al. |
| 5,866,210 A | 2/1999 | Rosynsky et al. |
| 5,882,573 A | 3/1999 | Kwok et al. |
| 5,902,540 A | 5/1999 | Kwok |
| 5,904,298 A | 5/1999 | Kwok et al. |
| 5,916,393 A | 6/1999 | Shaffer et al. |
| 5,921,476 A | 7/1999 | Akin et al. |
| 5,939,136 A | 8/1999 | Cronk et al. |
| 6,033,513 A | 3/2000 | Nakamura |
| 6,067,928 A | 5/2000 | Holzer, Jr. et al. |
| 6,077,373 A | 6/2000 | Fletcher et al. |
| 6,077,375 A | 6/2000 | Kwok |
| D433,692 S | 11/2000 | Fort et al. |
| 6,235,137 B1 | 5/2001 | Van Eperen et al. |
| 6,248,097 B1 | 6/2001 | Beitz et al. |
| 6,250,357 B1 | 6/2001 | Niedermeyer |
| 6,253,957 B1 | 7/2001 | Messerly et al. |
| 6,289,841 B1 | 9/2001 | Caldwell |
| 6,291,016 B1 | 9/2001 | Donges et al. |
| 6,296,463 B1 | 10/2001 | Allen |
| 6,311,899 B1 | 11/2001 | Hidaka et al. |
| 6,361,634 B1 | 3/2002 | White et al. |
| 6,378,784 B1 | 4/2002 | Allen et al. |
| 6,383,568 B1 | 5/2002 | Gast-Bray |
| 6,422,428 B1 | 7/2002 | Allen et al. |
| 6,435,425 B1 | 8/2002 | Saidman |
| 6,436,216 B1 | 8/2002 | Grover |
| 6,509,089 B1 | 1/2003 | Rollins et al. |
| 6,537,373 B1 | 3/2003 | Kitano et al. |
| 6,579,382 B2 | 6/2003 | Ito |
| 6,589,601 B1 | 7/2003 | Shimada |
| 6,652,693 B2 | 11/2003 | Burriss et al. |
| 6,676,038 B2 | 1/2004 | Gressett, Jr. et al. |
| 6,696,147 B1 | 2/2004 | Herring, Jr. et al. |
| 6,719,846 B2 | 4/2004 | Nakamura et al. |
| 6,745,948 B1 | 6/2004 | Hidaka et al. |
| 6,814,555 B2 | 11/2004 | Allen |
| 6,840,404 B1 | 1/2005 | Schultz et al. |
| 6,855,373 B2 | 2/2005 | Karlsson |
| 6,863,225 B2 | 3/2005 | Nakamura |
| 6,905,081 B2 | 6/2005 | Saidman et al. |
| 6,911,232 B2 | 6/2005 | Crane et al. |
| 6,926,772 B2 | 8/2005 | Leonard |
| 6,932,802 B2 | 8/2005 | Luizzi, Jr. et al. |
| 6,936,125 B2 | 8/2005 | Harris |
| 7,014,911 B2 | 3/2006 | Harris |
| D519,536 S | 4/2006 | de Leeuw et al. |
| D521,035 S | 5/2006 | de Leeuw et al. |
| D529,321 S | 10/2006 | Gould et al. |
| 7,118,558 B2 | 10/2006 | Wu et al. |
| 7,152,815 B2 | 12/2006 | Harris et al. |
| D536,354 S | 2/2007 | Kufner et al. |
| 7,175,108 B2 | 2/2007 | Saine |
| 7,255,292 B2 | 8/2007 | Saidman |
| D550,261 S | 9/2007 | Bondeson et al. |
| 7,320,814 B2 | 1/2008 | Blincoe et al. |
| 7,374,792 B2 | 5/2008 | Rosynsky et al. |
| 7,438,763 B2 | 10/2008 | Kanke |
| 7,462,240 B2 | 12/2008 | Harris et al. |

(56) References Cited

U.S. PATENT DOCUMENTS

| | | |
|---|---|---|
| 7,465,367 B2 | 12/2008 | Day |
| D588,617 S | 3/2009 | Burmester et al. |
| 7,521,087 B2 | 4/2009 | Rosynsky et al. |
| 7,541,068 B2 | 6/2009 | Tisone |
| 7,559,487 B2 | 7/2009 | Gressett, Jr. et al. |
| 7,578,882 B2 | 8/2009 | Harris et al. |
| D599,388 S | 9/2009 | Schreck |
| 7,647,885 B2 | 1/2010 | Crane et al. |
| 7,703,705 B2 | 4/2010 | Ganzer |
| 7,709,061 B2 | 5/2010 | Craamer et al. |
| 7,754,040 B2 | 7/2010 | Norrby |
| 7,798,434 B2 | 9/2010 | Bondeson et al. |
| 7,820,001 B2 | 10/2010 | Thomas et al. |
| 7,833,369 B2 | 11/2010 | Zhou et al. |
| 7,846,281 B2 | 12/2010 | Muvundamina |
| D641,767 S | 7/2011 | Juergens |
| D643,054 S | 8/2011 | Sennrich |
| 8,186,296 B2 | 5/2012 | Brown et al. |
| 8,445,061 B2 | 5/2013 | McGuffey |
| 9,409,199 B2 | 8/2016 | Nakano |
| 2001/0000611 A1 | 5/2001 | Cline et al. |
| 2001/0017102 A1 | 8/2001 | Caldwell |
| 2001/0022155 A1 | 9/2001 | Nakamura |
| 2001/0028920 A1 | 10/2001 | Ito et al. |
| 2001/0030014 A1 | 10/2001 | Kwok |
| 2001/0053420 A1 | 12/2001 | Donges et al. |
| 2001/0054477 A1 | 12/2001 | Kwok |
| 2002/0036050 A1 | 3/2002 | Kwok |
| 2002/0134858 A1 | 9/2002 | Gressett et al. |
| 2002/0136833 A1 | 9/2002 | Riney |
| 2002/0138064 A1 | 9/2002 | Datta et al. |
| 2003/0089447 A1 | 5/2003 | Molee et al. |
| 2003/0104130 A1 | 6/2003 | Karlsson |
| 2003/0161955 A1 | 8/2003 | Brumwell |
| 2003/0161964 A1 | 8/2003 | Leonard |
| 2003/0173018 A1 | 9/2003 | Harris |
| 2003/0173024 A1 | 9/2003 | Hayder et al. |
| 2003/0224105 A1 | 12/2003 | Chondroudis et al. |
| 2004/0159672 A1 | 8/2004 | Auber et al. |
| 2004/0164180 A1 | 8/2004 | Harris et al. |
| 2005/0013975 A1 | 1/2005 | Brock et al. |
| 2005/0015050 A1 | 1/2005 | Mowery et al. |
| 2005/0137549 A1 | 6/2005 | Lindsay et al. |
| 2005/0271806 A1 | 12/2005 | Ganzer et al. |
| 2006/0251806 A1 | 11/2006 | Brock et al. |
| 2006/0254698 A1 | 11/2006 | Tachibana et al. |
| 2006/0258249 A1 | 11/2006 | Fairbanks et al. |
| 2007/0131335 A1 | 6/2007 | Zhou et al. |
| 2007/0135008 A1 | 6/2007 | Hall et al. |
| 2008/0145530 A1 | 6/2008 | Bondeson et al. |
| 2008/0245298 A1 | 10/2008 | Ayers |
| 2008/0302299 A1 | 12/2008 | Lessley et al. |
| 2009/0062761 A1 | 3/2009 | Goerg-Wood et al. |
| 2009/0206506 A1 | 8/2009 | Crane et al. |
| 2010/0024987 A1 | 2/2010 | Saine et al. |
| 2010/0221435 A1 | 9/2010 | Fork et al. |
| 2010/0221449 A1 | 9/2010 | Schlatterbeck et al. |
| 2010/0224121 A1 | 9/2010 | Klingel |
| 2010/0279127 A1 | 11/2010 | Ukai et al. |
| 2010/0297353 A1 | 11/2010 | Sahoda et al. |
| 2010/0327074 A1 | 12/2010 | Bondeson et al. |
| 2011/0012752 A1 | 1/2011 | Ferrar |
| 2011/0014369 A1 | 1/2011 | McGuffey |
| 2011/0014430 A1 | 1/2011 | McGuffey |
| 2011/0114266 A1 | 5/2011 | Petersen et al. |
| 2011/0139066 A1 | 6/2011 | Chuang et al. |
| 2012/0258246 A1 | 10/2012 | Saine et al. |

FOREIGN PATENT DOCUMENTS

| | | |
|---|---|---|
| EP | 0112638 A2 | 7/1984 |
| EP | 0322538 A1 | 7/1989 |
| EP | 0372120 A2 | 6/1990 |
| EP | 0380781 | 8/1990 |
| EP | 0411287 A1 | 2/1991 |
| EP | 0792744 A2 | 9/1997 |
| EP | 1176232 A1 | 1/2002 |
| EP | 1880772 A1 | 1/2008 |
| EP | 2679313 A2 | 1/2014 |
| GB | 1444073 | 7/1976 |
| GB | 1455469 A | 11/1976 |
| GB | 2118021 A | 10/1983 |
| JP | 61152801 | 7/1986 |
| JP | 11244774 | 9/1999 |
| JP | 2001259497 A | 9/2001 |
| JP | 2001347209 A | 12/2001 |
| JP | 2004249191 A | 9/2004 |
| JP | 2004352494 A | 12/2004 |
| JP | 2009011890 A | 1/2009 |
| WO | 1993008924 A1 | 5/1993 |
| WO | 9604874 A1 | 2/1996 |
| WO | 9954057 A1 | 10/1999 |
| WO | 0066351 A2 | 11/2000 |
| WO | 02098572 A1 | 12/2002 |
| WO | 2011009913 A1 | 1/2011 |
| WO | 2011083644 A1 | 7/2011 |

OTHER PUBLICATIONS

European Patent Office, European Search Report in EP Application No. 04001330, Feb. 19, 2007.

European Patent Office, International Search Report and Written Opinion in PCT Application Serial No. PCT/US2012/032893, Aug. 8, 2012.

European Patent Office, Written Opinion of the International Preliminary Examining Authority in PCT Application Serial No. PCT/US2012/032893, May 7, 2013.

European Patent Office, International Preliminary Report on Patentability in PCT Application Serial No. PCT/US2012/032893, Aug. 9, 2013.

European Patent Office, European Search Report in EP Application Serial No. 13163420.6-1760, Feb. 4, 2015 (12 pages).

European Patent Office, Communication Pursuant to Article 94(3) EPC in EP Application SerialNo. 12 716 903-.5—1760, Jun. 12, 2015 (4 pages).

H.B. Fuller, Fiche Technique Technical Data Sheet, NW 1028 Zeropack®, Hotmelt Adhesive, Oct. 2005.

ITW Dynatec™, Integra Elastic Strand Coating System, Website, 3 pgs., undated.

J&M Laboratories, Durastitch (TM) Technology, New Product Release Manual, Feb. 1997.

National Adhesives, Advesives Division, Product Data Sheet, DISPOMELT 757, 134-127C, Oct. 2007.

National Adhesives, EASYMELT® 34-375C, Nov. 3, 2005.

National Adhesives, EASYMELT® 34-897B, Jul. 1, 2008.

National Adhesives, EASYMELT® 34-901B, Jul. 1, 2008.

Nordson Corporation, Using Foamed Materials for Bonding and Sealing, Brochure, 2005.

Nordson Corporation, Nordson Debuts New Look, New Products at INDEX '99, trends published by Nordson Corporation for the Nonwovens Industry, vol. 11, No. 1, Apr. 1999, pp. 1-4.

Nordson Corporation, Quick-Reference, P/N 1072400A, Summit™Lamination Applications, 2006 (6 pages).

Rajiv S. Rao et al., Vibration and Stability in the Melt Blowing Process, Ind. Eng. Chem., 32, pp. 3100-3111, 1993.

Syang-Peng Rwei, Dog-Legging in the Melt Spinning Process, Polymer Engineering and Science, vol. 38, No. 2, pp. 341-347, Feb. 1998.

Chinese Application No. 2013-10125239.7: First Office Action with Search Report dated Jun. 14, 2016.

International Patent Application No. PCT/US2015/043713: International Preliminary Report dated Feb. 14, 2017, 7 pages.

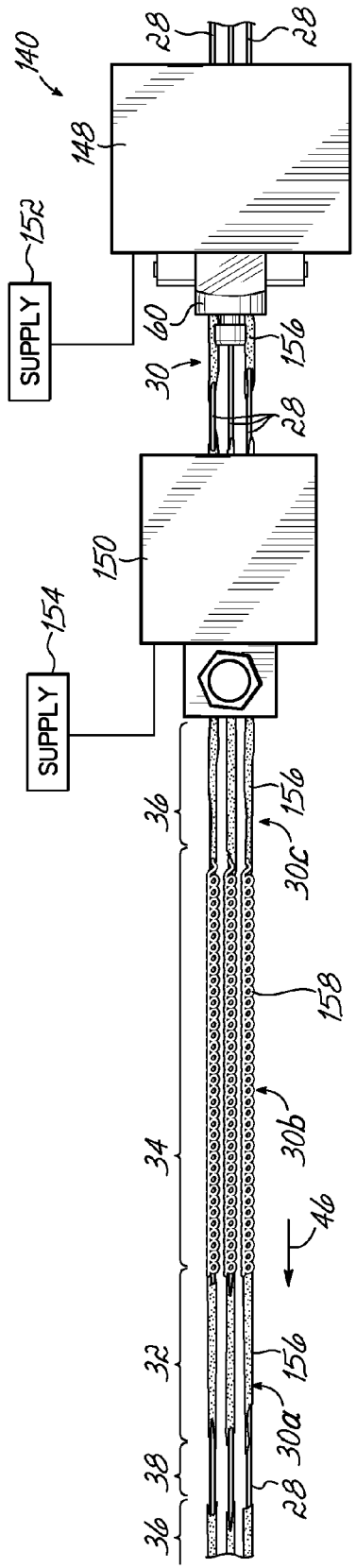
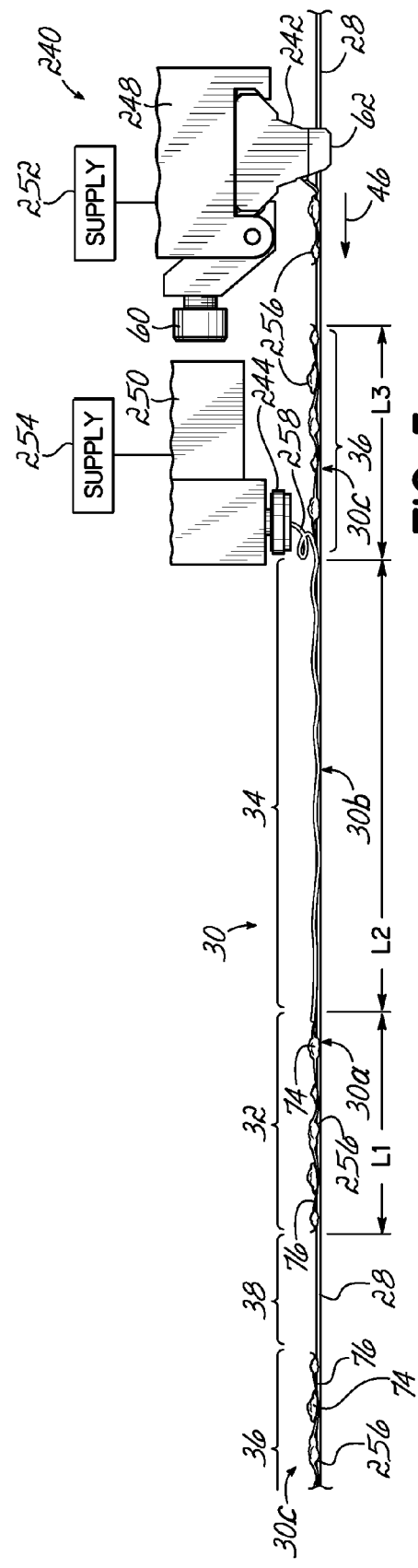

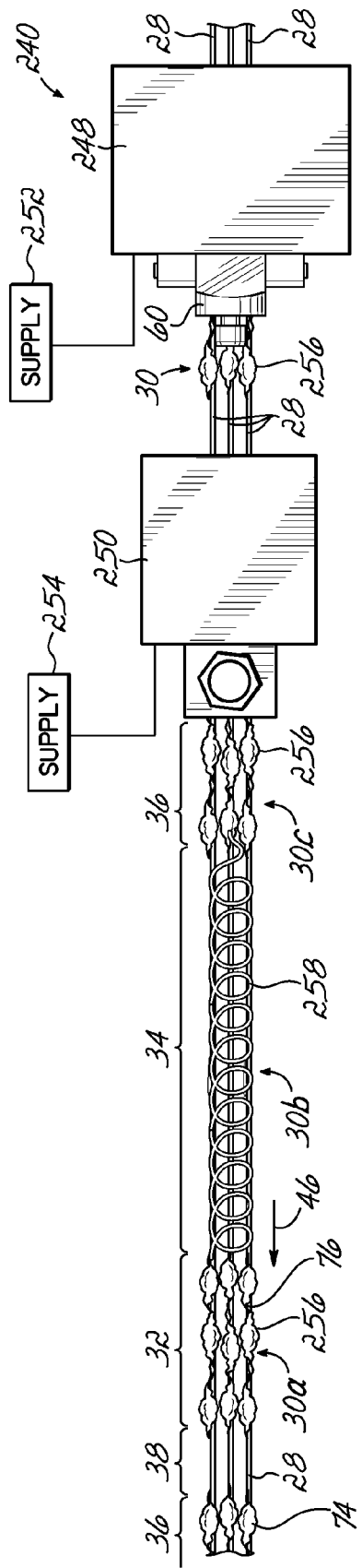
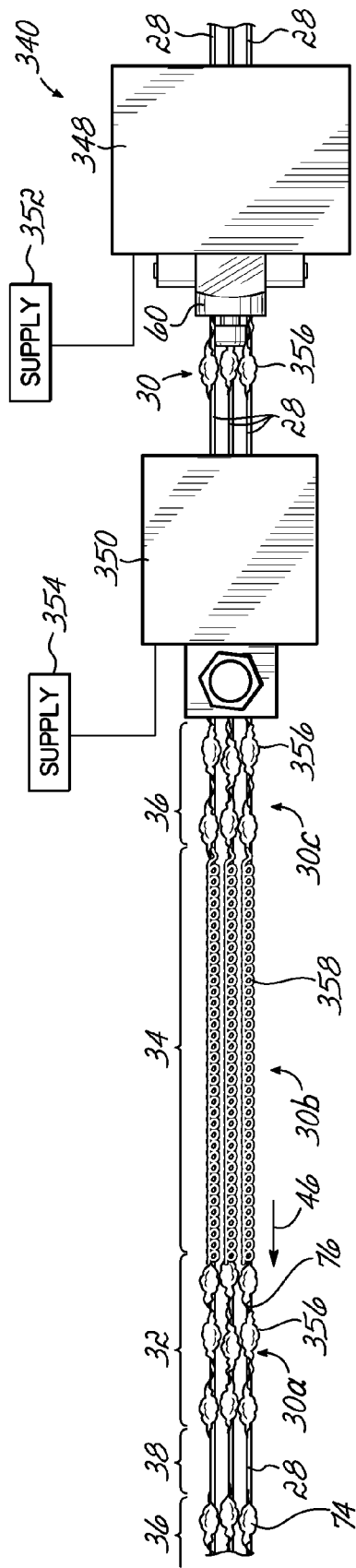
FIG. 6
FIG. 7

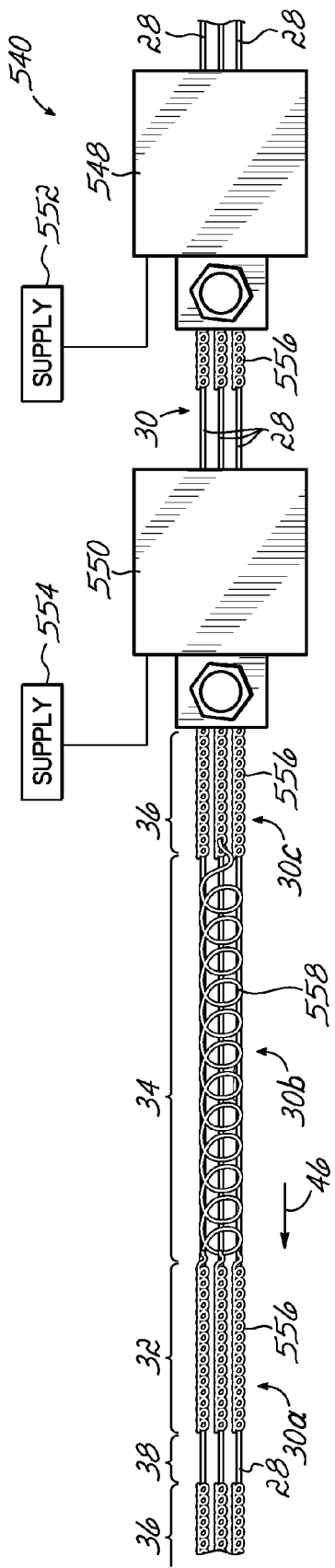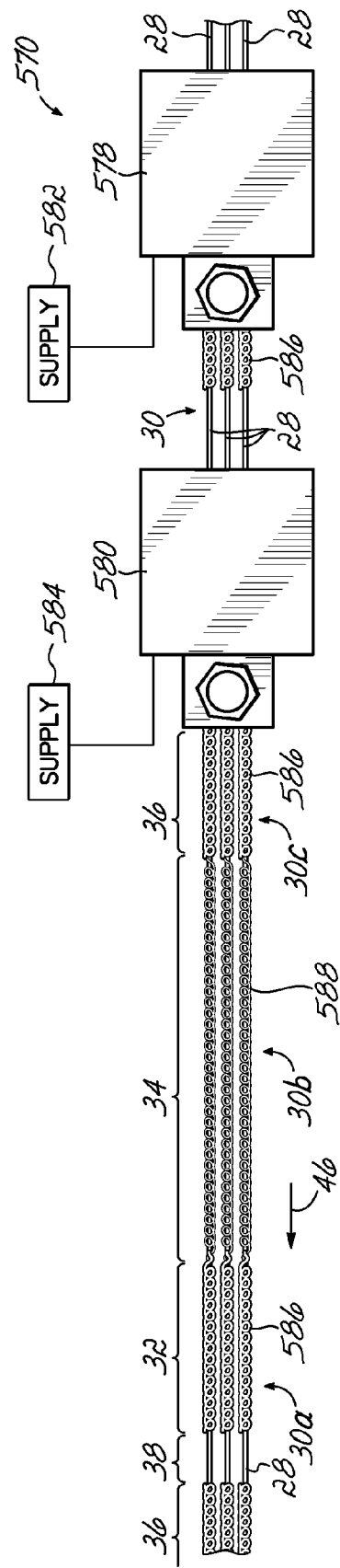

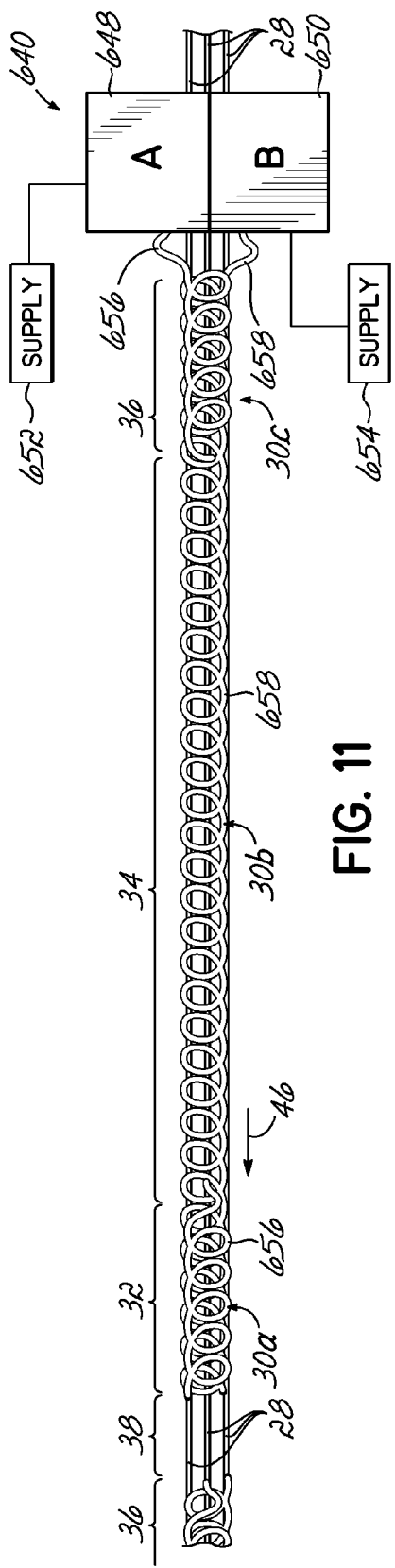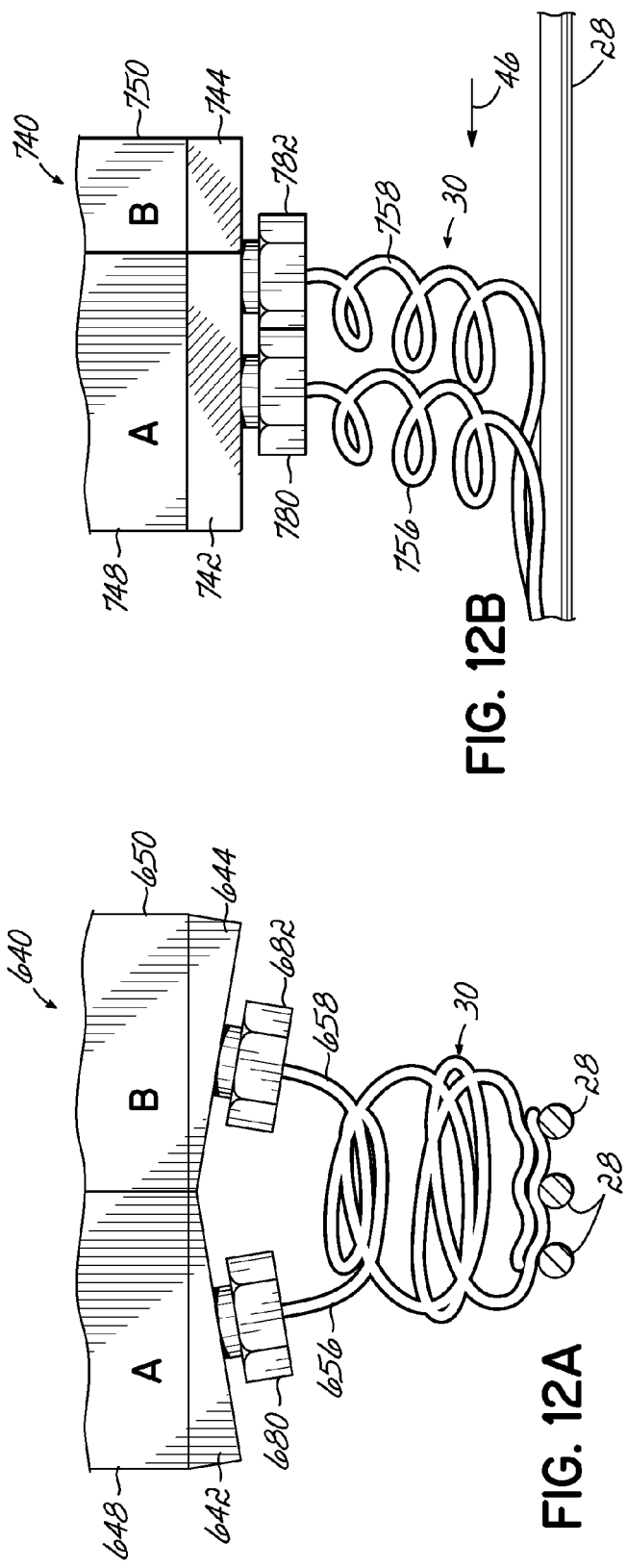
FIG. 11
FIG. 12B
FIG. 12A

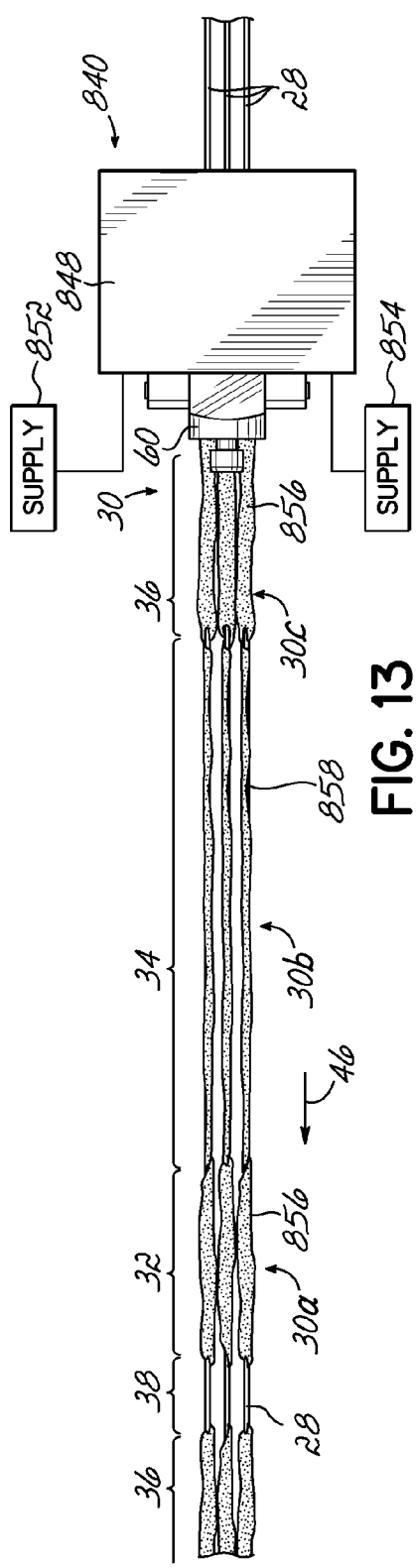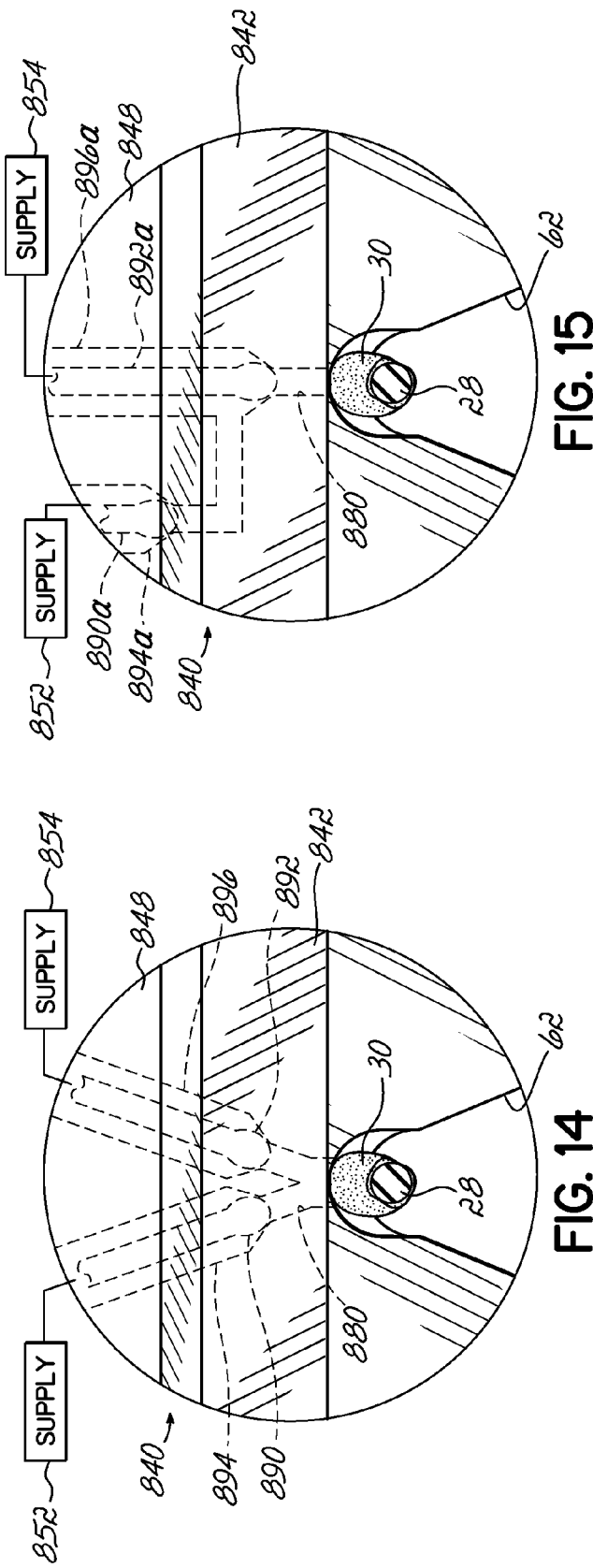
FIG. 13
FIG. 14
FIG. 15

METHOD FOR APPLYING VARYING AMOUNTS OR TYPES OF ADHESIVE ON AN ELASTIC STRAND

CROSS REFERENCE TO RELATED APPLICATIONS

This application is a continuation-in-part of U.S. patent application Ser. No. 14/644,318, filed on Mar. 11, 2015 (pending), which is a continuing application of U.S. patent application Ser. No. 14/456,418, filed on Aug. 11, 2014 (issued as U.S. Pat. No. 9,067,394 on Jun. 30, 2015) which is a continuation-in-part of U.S. patent application Ser. No. 13/444,126, filed on Apr. 11, 2012 (issued as U.S. Pat. No. 9,034,425 on May 19, 2015), the disclosures of which are incorporated by reference herein in their entirety.

This application is also a continuation-in-part of U.S. patent application Ser. No. 14/644,326, filed on Mar. 11, 2015 (pending), which is a divisional application of U.S. patent application Ser. No. 13/444,126, filed on Apr. 11, 2012 (issued as U.S. Pat. No. 9,034,425 on May 19, 2015), the disclosures of which are incorporated by reference herein in their entirety.

TECHNICAL FIELD

The present invention generally relates to a method and devices for dispensing adhesive and more particularly, to a method and devices for dispensing adhesive onto at least one elastic strand during construction of a personal disposable hygiene product.

BACKGROUND

Liquid adhesive, such as hot melt adhesive, is applied onto various components during manufacture of disposable personal hygiene products such as diapers, adult incontinence products, and feminine hygiene products. Dispensing methods and systems have been developed for applying hot melt adhesive onto various components of the disposable personal hygiene product. In one example, these dispensing systems apply a hot melt adhesive filament to one or more stretched elastic strands, which are then adhered to a nonwoven substrate to form an elasticized portion of the disposable personal hygiene product. Downstream of the dispensing system, the various components (e.g., flat substrate layers and elastic strands) pass through a pressure nip to secure the components together.

Many disposable personal hygiene products include elasticized leg gathers adjacent to leg openings to secure the personal hygiene product against the user's legs and to contain any waste material captured by the personal disposable hygiene product. In these applications, a high level of creep resistance is desirable. "Creep" of an elastic strand is defined as the movement of either end of the elastic strand from an initial location where the end is adhered to a substrate. If an elastic strand undergoes any significant amount of creep after assembly, at least one end of the elastic strand will effectively de-bond from the substrate and reduce the ability of the elasticized portion to remain firmly engaged with the skin surface. To avoid this undesirable creep, a high quality bond must be formed by the adhesive applied to the elastic strand so that the elastic strand does not de-bond from the substrate.

One well understood method of improving the quality of an adhesive bond and thereby reducing creep is by applying additional adhesive on the substrate or the elastic strand(s). However, applying too much adhesive to the elastic strand locks the elastic strand along its length and thereby reduces the effectiveness of the elastic material to apply force to the substrate. In other words, the elastic strand loses the ability to apply sufficient retraction force to the substrate. Moreover, increasing the amount of adhesive used in disposable personal hygiene product manufacturing significantly increases cost and also reduces the "hand" or softness of the resulting product. Applying too much adhesive material may also lead to "burn through," which occurs when the adhesive material burns or melts through the adhered substrate. Consequently, the amount of adhesive used to adhere elastic strands to substrates should be minimized while also maintaining a high level of creep resistance, a high retraction force, and minimized burn through and stiffness.

However, conventional dispensing methods and systems for coating elastic strands in personal disposable hygiene products utilize a constant volume or coating of adhesive along the entire length of the elastic strand(s). As described above, the coating must be sufficient to prevent creep at the opposing ends of the elastic strand(s), and thus, the constant coating adds significant add on weight to the final personal disposable hygiene product. As described above, any excess adhesive add on is undesirable for multiple reasons, including reduced force retraction capability and softness and increased manufacturing cost. Furthermore, the same type of adhesive material must be used for the entire length of the elastic strand(s), and so-called elastic attachment adhesives are more expensive than general construction glues. Accordingly, the waste of additional adhesive material can add significant cost to the production of the end product with the elastic stand(s), in this case, the disposable personal hygiene product.

There is a need, therefore, for an adhesive dispensing method and apparatus that addresses one or more of these difficulties and reduces the amount of adhesive used to form elasticized portions of personal disposable hygiene products.

SUMMARY

According to one embodiment of the invention, a method of dispensing adhesive onto a stretched elastic strand during the manufacturing of personal disposable hygiene products includes moving the elastic strand in a machine direction and delivering first and second adhesive streams, from corresponding first and second adhesive supplies, through a module and into a dispensing nozzle. The first and second adhesive streams remain separated during movement through the module and into the nozzle. The flow of the first and second adhesive streams is controlled to cause dispensing of adhesive at the nozzle, with the dispensing including applying first, second, and third volumes of adhesive onto respective first, second, and third portions of the elastic strand. The second and third portions are located downstream from the first portion in the machine direction, and the second volume of adhesive is less than each of the first and third volumes of adhesive. The stretched elastic strand is then contacted with first and second substrate layers to adhesively secure the elastic strand with the substrate layers, and the elastic strand is released to allow retraction from the stretched condition, thereby collectively defining an elasticized portion of the hygiene product with the first and second substrate layers. The first and third portions of the elastic strand define opposing ends of the elastic strand when bonded to the substrate layers, with the first and third volumes of adhesive limiting movement of the opposing ends relative to the substrate layers while maintaining the bond therebetween. The second portion of the elastic strand defines a central portion extending between the opposing ends when bonded to the substrate layers, with the second volume of adhesive being sufficiently low to allow the elastic strand to retract from the stretched condition. The maintained separation between the first and second adhesive streams avoids pressure differences from adversely affecting the operation of valves or other control structures controlling the dispensing of adhesive, and this arrangement also enables different adhesive materials to be used, and/or wet-on-wet contact dispensing of adhesive, in certain aspects.

It will be understood that the term "module" in this context refers generally to the applicator element(s) that supply and control flow of the adhesive streams into the nozzle, and it is well understood that such element(s) may take multiple forms depending on the user and the desired dispensing system and process. Examples of such element(s) defining the "module" are described in further detail below.

In another embodiment, a method of dispensing adhesive onto a stretched elastic strand during the manufacturing of personal disposable hygiene products includes moving the elastic strand in a machine direction and delivering first and second adhesive streams, from corresponding first and second adhesive supplies, through a module and into a dispensing nozzle. The first adhesive stream consists of a first type of adhesive material and the second adhesive stream consists of a second type of adhesive material which is different than the first type of adhesive material. The first and second adhesive streams remain separated during movement through the module and into the nozzle. The flow of the first and second adhesive streams is controlled to cause dispensing of adhesive at the nozzle, with the dispensing including applying the first adhesive stream of adhesive onto a first portion of the elastic strand; applying the second adhesive stream onto a second portion of the elastic strand located downstream from the first portion in the machine direction; and applying the first adhesive stream onto a third portion of the elastic strand located downstream from the second portion in the machine direction. The stretched elastic strand is then contacted with first and second substrate layers to adhesively secure the elastic strand with the substrate layers, and the elastic strand is released to allow retraction from the stretched condition, thereby collectively defining an elasticized portion of the hygiene product with the first and second substrate layers. The first and third portions of the elastic strand define opposing ends of the elastic strand when bonded to the substrate layers, with the first type of adhesive limiting movement of the opposing ends relative to the substrate layers while maintaining the bond therebetween. The second portion of the elastic strand defines a central portion extending between the opposing ends when bonded to the substrate layers, with the second type of adhesive allowing the elastic strand to retract from the stretched condition. In one example, the first type of adhesive is an elastic attachment adhesive having high bond strength, while the second type of adhesive is a conventional construction glue which is less expensive than the elastic attachment adhesive.

In a further embodiment, a dispensing apparatus is configured to apply adhesive to a stretched elastic strand to be adhered to a substrate to form a personal disposable hygiene product. The dispensing apparatus includes a module with a first passage terminating at a first module outlet and configured to communicate with a first adhesive supply to receive a first adhesive stream, and a second passage terminating at a second module outlet and configured to communicate with a second adhesive supply so as to receive a second adhesive stream. The first and second passages are separated in the module such that the first and second adhesive streams remain separated during movement through the module. The apparatus also includes a dispensing nozzle coupled to the module and including first and second nozzle inlets communicating with the first and second module outlets, respectively, as well as at least one nozzle outlet for dispensing adhesive onto the elastic strand. The apparatus further includes first and second valves which open and close to control flow of the first and second adhesive streams, respectively, through the module and into the nozzle. These valves control dispensing of adhesive onto the elastic strand such that first, second, and third volumes of adhesive are applied onto respective first, second, and third portions of the elastic strand, with the second portion of the elastic strand being between the first and third portions and the second volume of adhesive being less than each of the first and third volumes of adhesive. The first and third portions of the elastic strand define opposing ends of the elastic strand when adhered to the substrate, while the second portion of the elastic strand defines a central portion extending between the opposing ends when adhered to the substrate. Once again, the maintained separation between the first and second adhesive streams avoids pressure differences from adversely affecting the operation of valves or other control structures controlling the dispensing of adhesive, while enabling additional aspects such as wet-on-wet contact dispensing and/or the use of different adhesive materials for the first and second adhesive streams.

In accordance with another embodiment, a contact dispensing nozzle is configured to apply adhesive to a stretched elastic strand moving in a machine direction. The nozzle includes a nozzle body having a front side, a rear side, and a slot for receiving the elastic strand which extends between the front and rear sides while defining a strand guide portion for guiding movement of the elastic strand along the machine direction. The nozzle also includes a first adhesive passage formed in the nozzle body which extends between a first nozzle inlet and a first nozzle outlet. The first nozzle inlet is configured to receive a first adhesive stream from a first adhesive supply, and the first nozzle outlet communicates with the slot to deliver the first adhesive stream into contact with the elastic strand. The nozzle further includes a second adhesive passage formed in the nozzle body which extends between a second nozzle inlet and a second nozzle outlet. The second nozzle inlet is configured to receive a second adhesive stream from a second adhesive supply, and the second nozzle outlet communicates with the slot downstream from the first nozzle outlet to deliver the second adhesive stream into contact with the elastic strand. The first and second adhesive passages maintain separation between the first and second adhesive streams during flow through the nozzle, which provides advantageous benefits as described above and throughout this document. The nozzle may also include, in some aspects, an air outlet for discharging pressurized air towards the adhesive in contact with the strand in order to spread the adhesive around a periphery of the strand, as well as first and second expansion chambers enabling die swell of adhesive upon exit from the first and second nozzle outlets.

Various additional features and advantages of the invention will become more apparent to those of ordinary skill in the art upon review of the following detailed description of the illustrative embodiments taken in conjunction with the accompanying drawings.

BRIEF DESCRIPTION OF THE DRAWINGS

FIG. 4 is a schematic top view of another embodiment of a dispensing apparatus for applying adhesive to elastic strands.

FIG. 5 is a schematic side view of another embodiment of a dispensing apparatus for applying adhesive to elastic strands.

FIG. 6 is a schematic top view of the dispensing apparatus of FIG. 5.

FIG. 7 is a schematic top view of yet another embodiment of a dispensing apparatus for applying adhesive to elastic strands.

FIG. 9 is a schematic top view of yet another embodiment of a dispensing apparatus for applying adhesive to elastic strands.

FIG. 10 is a schematic top view of yet another embodiment of a dispensing apparatus for applying adhesive to elastic strands.

FIG. 11 is a schematic top view of another embodiment of a dispensing apparatus for applying adhesive to elastic strands, the dispensing apparatus including two nozzles in parallel.

FIG. 12A is a schematic front view of the dispensing apparatus of FIG. 11 during a dispensing operation.

FIG. 12B is a schematic side view of another embodiment of a dispensing apparatus similar to the dispensing apparatus of FIGS. 11 and 12A.

FIG. 13 is a schematic top view of yet another embodiment of a dispensing apparatus for applying adhesive to elastic strands.

FIG. 14 is a schematic front view of the dispensing apparatus of FIG. 13, showing a first set of valves in phantom.

FIG. 15 is a schematic front view of the dispensing apparatus of FIG. 13, showing a second set of valves in phantom.

DETAILED DESCRIPTION

Various embodiments of dispensing apparatus and associated methods are described below for applying adhesive to a stretched elastic strand so that the elastic strand can be adhered to one or more substrates in the manufacturing of an elasticized portion of a personal disposable hygiene product (such as a diaper). Each of the embodiments is capable of operating such that a higher volume of adhesive is provided on first and third portions of the elastic strand, which become the opposing ends of the elastic strand on the hygiene product and must be secured in position against creep forces, compared to the second portion of the elastic strand which defines a central portion between the opposing ends. This advantageously limits the amount of adhesive necessary to produce the hygiene product when compared to conventional systems and methods using continuous, uniform coatings of adhesive on elastic strands. Furthermore, although such dispensing methods can be achieved with multiple modules and multiple nozzles as set forth in several embodiments below, it has been discovered by the current inventors that performing such volume (per unit length of strand) variations with less overall equipment, such as a single module and single dispensing nozzle, provides further benefits such as equipment and maintenance cost savings. These embodiments, which include those described with reference to FIGS. 13 through 24 below, are configured to provide and dispense first and second adhesive streams to produce the varying volumes in both contact and non-contact dispensing settings. Additionally, these embodiments also enable use of different types of adhesive materials for the strand portions instead of differing volumes, in one acceptable alternative, and there is also no pressure difference that must be overcome by valves or other control elements to accurately control the dispensing of both the first and second adhesive streams when combined in a single applicator manifold (or "module" as set forth below). Therefore, the invention as set forth in the embodiments below provides numerous advantages and benefits compared to conventional dispensing apparatus and methods for applying adhesive in the manufacturing of hygiene products.

Figure 1:
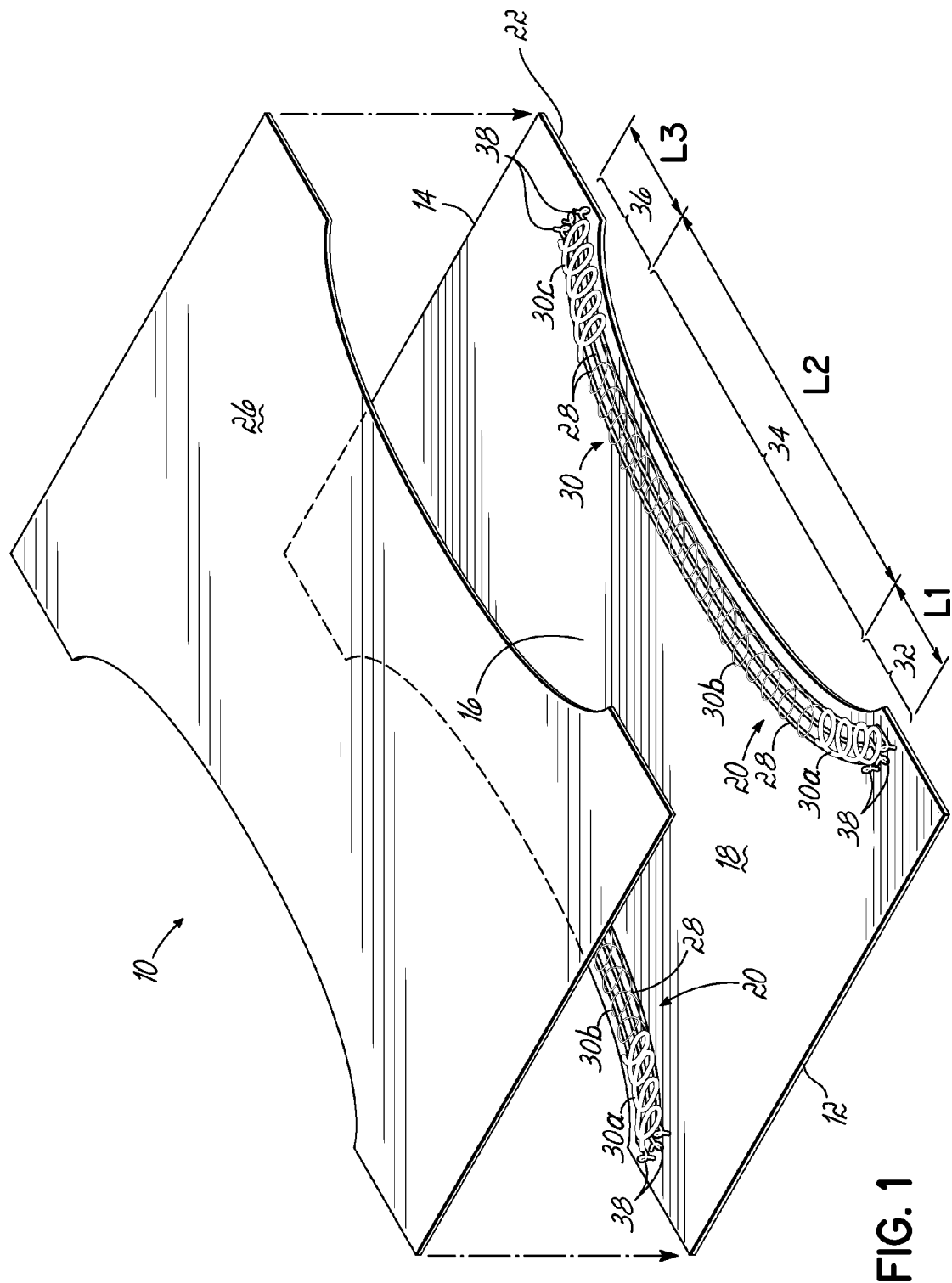
FIG. 1 is a partially exploded perspective view of a personal disposable hygiene product according to one embodiment of the current invention.

Turning now with specific reference to the Figures, FIG. 1 illustrates one embodiment of a disposable personal hygiene product 10 manufactured using an exemplary method and apparatus of the invention. The disposable personal hygiene product 10 of this embodiment is a disposable diaper 10 including first and second ends 12, 14 configured to wrap around the waist of the user and a central portion 16 configured to extend between the legs of the user. The diaper 10 includes a flat nonwoven substrate 18, leg gathers 20 formed along each longitudinal side 22, 24 of the diaper 10 between the first and second ends 12, 14, and a second flat substrate 26 secured to the nonwoven substrate 18 to enclose the leg gathers 20. The second flat substrate 26 is another nonwoven substrate in the illustrated embodiment, although it will be understood that the elastic strands 28 may instead be sandwiched between (and adhesively secured with) two folded-over substrate layers of the same flat substrate in other embodiments consistent with the invention. The leg gathers 20 are formed by one or more elastic strands 28 that are secured to the nonwoven substrate 18 in a stretched condition so as to provide the diaper 10 with elasticity around the legs of the user, and the elasticity is provided when the elastic strands 28 are released to reduce tension in the elastic strands 28 and allow the elastic strands 28 to retract from a stretched condition following contacting and adhesive bonding to the substrate(s). The nonwoven substrate 18, leg gathers 20, and second substrate 26 are secured to each other with hot melt adhesive 30.

More particularly, each of the elastic strands 28 is advantageously adhered to the nonwoven substrate 18 by a varying amount of hot melt adhesive 30 applied along the length of the elastic strand 28. As described in further detail below, this varying amount of adhesive 30 may be applied by first and second dispensing nozzles in series, wherein the first dispensing nozzle may include a strand guide in some embodiments while the second dispensing nozzle cannot include a strand guide. To this end, each elastic strand 28 includes a first portion 32 adjacent the first end 12, a second portion 34 extending from the first portion 32 and adjacent the central portion 16, and a third portion 36 located adjacent to the second portion 34 and the second end 14. To this end, the first and third portions 32, 36 define opposing ends of the elastic strand 28 when adhered to the nonwoven substrate 18, while the second portion 34 defines a central portion of the elastic strand 28 during adherence. The first portion 32 is coated with a first volume of adhesive 30a, the second portion 34 is coated with a second volume of adhesive 30b, and the third portion 36 is coated with a third volume of adhesive 30c. The second volume of adhesive 30b is less than each of the first and third volumes of adhesive 30a, 30c. As well understood, the elastic strands 28 also include small free ends 38 beyond the first and second end portions 32, 34 that are not coated with adhesive 30 and thus retract or curl up when the remainder of the elastic strands 28 is adhered to the substrate 18. In the preceding and following description, the term "volume" is used as shorthand to describe an average volume of adhesive per unit length over the corresponding strand portion. Thus, the average volume of adhesive per unit length applied to the first and third portions 32, 36 of the elastic strand 28 is higher than the average volume of adhesive per unit length applied to the second portion 34.

With continued reference to FIG. 1, the higher first and second volumes of adhesive 30a, 30c along the first and third portions 32, 36 are schematically shown as a thicker spiral filament while a thinner spiral filament is shown at the second portion 34 to indicate the lessened second volume of adhesive 30b. It will be appreciated that the actual pattern applied to the elastic strands 28 may vary in other embodiments, such as by being applied as a plurality of discrete masses of adhesive that produce discrete bond points when adhering the elastic strands 28 to the nonwoven substrate 18. It will also be understood that while the volume per unit length is described as roughly constant over the entire length of a corresponding strand portion 32, 34, 36 in the exemplary embodiments below, the volume per unit length may vary over the length of one or more of the strand portions 32, 34, 36 without departing from the scope of the invention (i.e., as long as the "volume" or average volume per unit length remains lesser for the second portion 34 than the first and third portions 32, 36). In addition, the adhesive application patterns shown in FIG. 1 and the following figures on the elastic strands 28 are schematic artist's renderings of these patterns, as it will be understood that these patterns may vary in appearance significantly in a practical setting.

Also as shown in FIG. 1, the first portion 32 of the elastic strand 28 defines a first length L1, the second portion 34 defines a second length L2, and the third portion 36 defines a third length L3. The second length L2 is larger than the first and third lengths L1, L3 combined so that the second volume of adhesive 30b is applied over a majority of the total length of the elastic strand 28. Thus, the first and third volumes of adhesive 30a, 30c, each of which is high enough to produce a high quality bond with desirable creep resistance, are only applied onto the first and third portions 32, 36 of the elastic strand 28 where such a level of creep resistance is necessary. This higher average volume of adhesive per unit length is not used in the second portion 34 of the elastic strand 28 where creep resistance is less of a concern. Considering that this second portion 34 includes a majority of the elastic strand 28, the total amount of adhesive 30 used to adhere the elastic strand 28 to the substrate 18 is significantly reduced compared to a constant coating over the entire length of the elastic strand 28. Thus, the diaper 10 of this embodiment advantageously minimizes the amount of adhesive add on necessary to produce a high quality bond or construction of the various components of the diaper 10.

Figure 2:
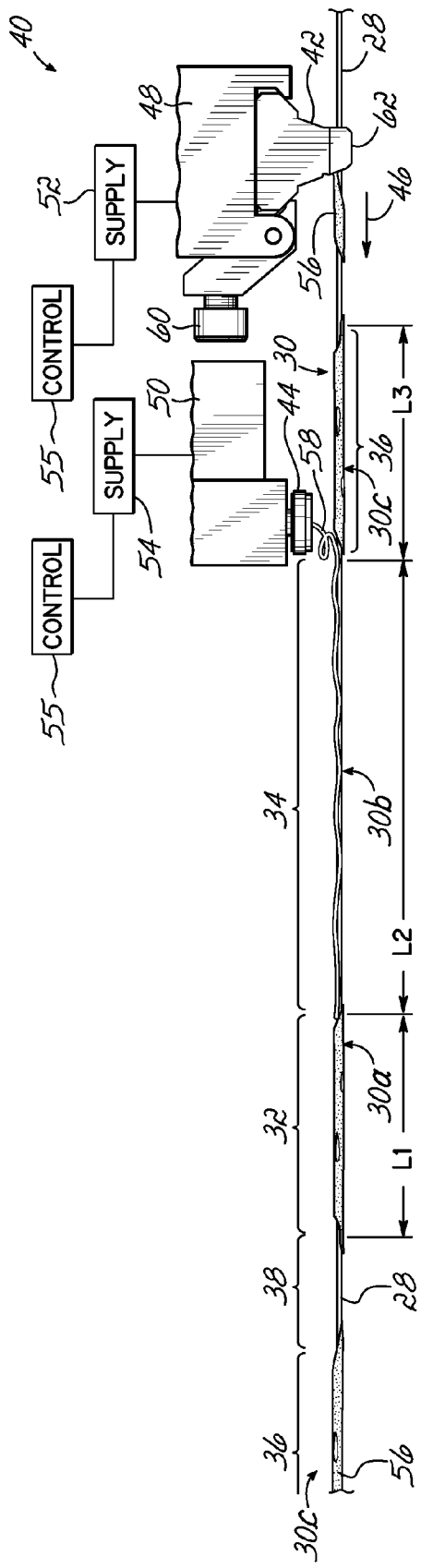
FIG. 2 is a schematic side view of a dispensing apparatus for applying adhesive to a plurality of stretched elastic strands according to one embodiment of the current invention.
Figure 3:
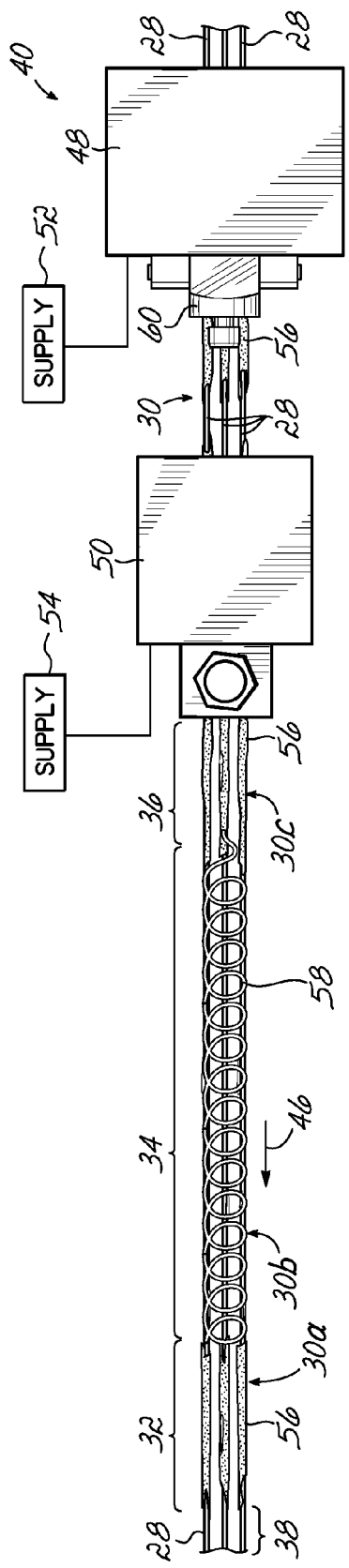
FIG. 3 is a schematic top view of the dispensing apparatus of FIG. 2.

Turning to FIGS. 2 and 3, one embodiment of a dispensing apparatus 40 is shown for producing the disposable personal hygiene product 10 described above. The dispensing apparatus 40 includes a first dispensing nozzle 42 and a second dispensing nozzle 44 arranged in series along a machine direction indicated by arrow 46. The plurality of elastic strands 28 moves along the machine direction 46 past the first dispensing nozzle 42 and then past the second dispensing nozzle 44. The first and second dispensing nozzles 42, 44 operate to dispense hot melt adhesive 30 onto the elastic strands 28 so as to coat the elastic strands 28 with the first, second, and third volumes of adhesive 30a, 30b, 30c as described above. As described in further detail below, the elastic strands 28 run continuously through the dispensing apparatus 40 and are cut into separate elastic strands 28 downstream from the dispensing apparatus 40. To enable this cutting separation, the adjacent free ends 38 of two elastic strands 28 in series are not coated with any adhesive material. Consequently, each of the first and second dispensing nozzles 42, 44 cycles on and off repeatedly during operation of the dispensing apparatus 40.

In the illustrated embodiment, the first dispensing nozzle 42 is incorporated into a first dispensing module 48 and the second dispensing nozzle 44 is incorporated into a second dispensing module 50 separate from the first dispensing module 48. In this embodiment, the first dispensing module 48 includes a contact nozzle and the second dispensing module includes a non-contact nozzle, each nozzle being configured to apply a filament, bead, coating, or other amount of adhesive (hereinafter referred to as a "quantity") to the elastic strands 28. More specifically, the first dispensing nozzle 42 shown is a contact nozzle as described in U.S. Patent Application No. 61/474,129 to Saine, filed Apr. 11, 2011 (which led to U.S. Pat. No. 9,168,554, issued on Oct. 27, 2015), which is assigned to the assignee of the current invention and the entire disclosure of which is hereby incorporated by reference herein. The second dispensing nozzle 44 shown is a non-contact swirl nozzle such as the Universal™ CF nozzle commercially available from Nordson Corporation of Westlake, Ohio, which is described in U.S. Pat. No. 4,785,996 to Ziecker et al., the entire disclosure of which is hereby incorporated by reference herein.

It will be understood that other types of non-contact nozzles (e.g., the Signature™ and Summitt™ Mini Swirl nozzles commercially available from Nordson Corporation of Westlake, Ohio) or other types of contact nozzles such as slot coaters may be used in other embodiments within the scope of this invention. Furthermore, even though the first and second dispensing nozzles 42, 44 are illustrated as different types of nozzles in this embodiment, it will be appreciated that the first dispensing nozzle 42 may be the same type of nozzle as the second dispensing nozzle 44 in other embodiments of the invention, assuming both dispensing nozzles 42, 44 are non-contact nozzles. Some of these alternatives are presented in further detail below with reference to FIGS. 4-12.

With continued reference to FIGS. 2 and 3, the first dispensing module 48 receives hot melt adhesive 30 from a first adhesive supply 52 and the second dispensing module 50 receives hot melt adhesive 30 from a second adhesive supply 54. The first and second adhesive supplies 52, 54 operate to pump heated liquid adhesive 30 to the first and second dispensing nozzles 42, 44. In one example, the first adhesive supply 52 includes a first individually adjustable pump 52 for supplying an adjustable flow of adhesive 30 to the first dispensing nozzle 42. The second adhesive supply 54 includes a second individually adjustable pump 54 separate from the first pump 52 for supplying another adjustable flow of adhesive 30 to the second dispensing nozzle 44. Alternatively, the first and second adhesive supplies 52, 54 may be first and second output streams of a common dual stream pump. In these embodiments with a dual stream pump, each adhesive supply 52, 54 delivers a predetermined flow of adhesive to each of the first and second dispensing nozzles 42, 44. Therefore, although the first and second adhesive supplies 52, 54 are illustrated as separate elements in FIGS. 2 and 3, it will be understood that the first and second adhesive supplies 52, 54 may be generated from a single dual stream pump or separate pumps without departing from the scope of the invention. Additionally, it will be understood that this and each of the following embodiments of the dispensing apparatus 40 may also include a control 55 for selectively actuating (e.g., turning on and off) the first and second adhesive supplies 52, 54.

The operation of the dispensing apparatus 40 is shown schematically in FIGS. 2 and 3. In this regard, the plurality of stretched, uncoated elastic strands 28 passes the first dispensing nozzle 42 while moving along the machine direction 46. The first dispensing nozzle 42 operates to dispense a first quantity 56 of adhesive onto each of the plurality of elastic strands 28. More specifically, a first quantity 56 is dispensed onto the first portion 32 and the third portion 36 of each elastic strand 28. As described in further detail in U.S. Patent Application No. 61/474,129 to Saine, the first quantity 56 is a quantity applied by contacting the elastic strand 28 with an extruded adhesive 30 and then blowing air onto the elastic strand 28 to spread the adhesive 30 around the elastic strand 28. As described briefly above, the elastic strands 28 are cut from a continuous elastic line stock downstream of the dispensing apparatus 40, so the first dispensing nozzle 42 cycles on and off to leave gaps with no adhesive 30 at the second portions 34 and at the free ends 38 between applications of adhesive to the first portions 32 and to the third portions 36.

In a similar manner, the plurality of elastic strands 28 coated with the first quantity 56 of adhesive then passes the second dispensing nozzle 44 while moving along the machine direction 46. The second dispensing nozzle 44 operates to dispense a second quantity 58 of adhesive onto the plurality of elastic strands 28 at the second portion 34. In this embodiment, the second quantity 58 is a filament forming a swirl pattern extending across all of the elastic strands 28. The second dispensing nozzle 44 is cycled on and off to apply the second quantity 58 onto the second portions 34 of the elastic strands 28, leaving the first and third portions 32, 36 and the free ends 38 substantially uncoated with the second quantity 58.

As shown schematically in FIGS. 2 and 3, the first quantity 56 of adhesive forms the first volume of adhesive 30a on the first portion 32 of each elastic strand 28 as well as the third volume of adhesive 30c on the third portion 36 of each elastic strand 28. The second quantity 58 of adhesive forms the second volume of adhesive 30b on the second portion 34 of each elastic strand 28. In this regard, the dispensing apparatus 40 operates to apply the first volume of adhesive 30a onto the first portion 32, apply the second volume of adhesive 30b onto the second portion 34, and apply the third volume of adhesive 30c onto the third portion 36. As described above, the first and third volumes of adhesive 30a, 30c are sufficient to provide a high quality bond with desirable creep resistance at the first and third portions 32, 36 of the elastic strands 28, while the second volume of adhesive 30b is less than the first or third volumes 30a, 30c of adhesive to advantageously minimize adhesive add on in the disposable personal hygiene product 10.

In one example, the first dispensing nozzle 42 is configured to dispense a coating that defines a volume (i.e., an average volume per unit length) of 0.2 g/m or 0.2 mg/mm on each elastic strand 28. The second dispensing nozzle 44 is configured to dispense a coating that defines a volume of 0.1 g/m or 0.1 mg/mm on each elastic strand 28. As a result, the first and third portions 32, 36 are coated with an equal volume of 0.2 mg/mm, while the second portion 34 is coated with a volume of 0.1 mg/mm. In other words, the first and third volumes of adhesive 30a, 30c are equivalent to 0.2 mg/mm and the second volume of adhesive 30b is equivalent to 0.1 mg/mm. Assuming approximate lengths of L1=L3=50 mm for the first and third portions 32, 36 and L2=300 mm for the second portion 34, the total adhesive add on per elastic strand is 50 mg of adhesive: (0.2 mg/mm)*(50 mm)=10 mg for each of the first and third portions 32, 36; plus (0.1 mg/mm)*(300 mm)=30 mg for the second portion 34.

By contrast, a conventional constant volume coating having the same bond strength at the first and third portions 32, 36 would require a volume of 0.2 mg/mm over the entire 400 mm length of the elastic strand, which equates to 80 mg of adhesive add on per strand. Thus, the dispensing apparatus 40 of the current invention advantageously reduces the adhesive add on by nearly 40% in this example compared to an analogous conventional coating. It will be understood that the relative values of the first, second, and third volumes 30a, 30b, 30c and the relative lengths of the strand portions 32, 34, 36 may be modified in other examples within the scope of the invention to produce adhesive savings of 40%-60% or even more, depending on the application. This level of adhesive reduction significantly reduces the manufacturing cost for each disposable personal hygiene product 10 and increases the hand or softness of the product 10 while maintaining the same high quality bonds as in conventional methods and dispensing apparatuses.

The first and second dispensing nozzles 42, 44 are controlled by internal valves (not shown in this embodiment) in the first and second dispensing modules 48, 50, as well understood in the art. These valves are operable to cycle on and off for the required lengths of time to dispense the first and second quantities 56, 58 onto enough continuous elastic strand stock to form 400-1500 products (diapers) per minute. Assuming the same portion lengths as described above with a 25 mm gap defining the free ends 38, the valves would operate as follows for producing 500 products (diapers) per minute. The valve of the first dispensing module 48 would open for about 14 milliseconds to apply adhesive 30 to each first portion 32 and each third portion 36, separated by closed times of about 85 milliseconds for each second portion 34 and about 7 milliseconds for each free end 38 location. The valve of the second dispensing module 50 would open for about 85 milliseconds to apply adhesive 30 to each second portion 34, separated by closed times of about 35 milliseconds for the other portions 32, 36, 38 of the elastic strands 28. It will be understood that the cycling rates of the valves may be modified in other embodiments without departing from the scope of the invention.

As described in further detail in U.S. Patent Application No. 61/474,129 to Saine, the first dispensing nozzle 42 may be connected to the first dispensing module 48 by a clamping mechanism 60 or a similar device. The first dispensing nozzle 42 defines a strand guide portion 62 for guiding each of the elastic strands 28 past the corresponding air and adhesive outlets (not shown) of the first dispensing nozzle 42. These strand guide portions 62 also align the plurality of strands 28 for passage under the air and adhesive outlets (not shown) of the second dispensing nozzle 44 because the second dispensing nozzle 44 cannot include a strand guide portion (e.g., such a strand guide portion would strip adhesive from the first dispensing nozzle 42 from the elastic strands 28). Further details of each of the first and second dispensing nozzles 42, 44 of this embodiment are described in the corresponding documents incorporated by reference above, and thus no further explanation of structure is provided here. It will be understood that in this and other embodiments described below, the first dispensing nozzle 42 may selectively include a strand guide portion 62, but the second dispensing nozzle 44 will not include a strand guide portion 62, regardless of the type of dispensing nozzles used in those embodiments. Examples of this arrangement are shown in FIGS. 2 and 5.

Although the embodiment of the dispensing apparatus 40 shown in FIGS. 2 and 3 is an exemplary embodiment of a dispensing apparatus for applying varying volumes of adhesive along the length of elastic strands 28, several modifications to the apparatus are also included within the scope of the current invention. With reference to FIG. 4, another embodiment of a dispensing apparatus 140 for applying varying volumes of adhesive along the length of elastic strands 28 in accordance with the invention is shown.

Similar to the previous embodiment, the dispensing apparatus 140 shown in FIG. 4 includes a first dispensing module 148 and a second dispensing module 150 arranged in series along the machine direction 46. The first dispensing module 148 of this embodiment includes a contact nozzle as described in U.S. Patent Application No. 61/474,129 to Saine. The second dispensing module 150 of this embodiment includes a non-contact swirl nozzle such as the Summitt™ Mini Swirl nozzle commercially available from Nordson Corporation of Westlake, Ohio, which is described in U.S. Pat. No. 4,815,660 to Boger, the entire disclosure of which is hereby incorporated by reference herein.

More particularly, and as described in further detail in U.S. Patent Application No. 61/474,129 to Saine, the first dispensing module 148 applies a first quantity 156 of adhesive, which is a quantity applied by contacting the elastic strand 28 with an extruded adhesive 30 and then blowing air onto the elastic strand 28 to spread the adhesive 30 around the elastic strand 28. The second dispensing module 150 applies a second quantity 158 of adhesive, which is a miniature swirled filament of adhesive 30, onto each elastic strand 28 individually. Thus, unlike the previous embodiment, each of the first and second dispensing modules 148, 150 in this embodiment apply adhesive 30 individually onto each elastic strand 28.

As shown in FIG. 4, the first and second dispensing modules 148, 150 receive adhesive material from corresponding adhesive supplies 152, 154. Similar to the embodiments described above, the adhesive supplies 152, 154 may include separate individually adjustable pumps for each dispensing module 148, 150 or a shared dual stream pump for both dispensing modules 148, 150. Similar to the previous embodiment, the first dispensing module 148 dispenses the first quantity 156 onto the first and third portions 32, 36 of the elastic strands 28, while the second dispensing module 150 dispenses the second quantity 158 onto the second portions 34 of the elastic strands 28 only. Thus, as shown by the adhesive patterns shown in FIG. 4, the first and third portions 32, 36 are coated with first and third volumes of adhesive 30a, 30c that are larger than a second volume of adhesive 30b coating the second portions 34. As with the previously described embodiment, the dispensing apparatus 140 advantageously applies a higher volume of adhesive 30 to the end portions 32, 36 of the elastic strands 28 than to the central portions 34, thereby significantly reducing adhesive use while maintaining similar high bond quality.

With reference to FIGS. 5 and 6, another embodiment of a dispensing apparatus 240 for applying varying volumes of adhesive along the length of elastic strands 28 in accordance with the invention is shown. Similar to the previous embodiment, the dispensing apparatus 240 shown in FIGS. 5 and 6 includes a first dispensing module 248 and a second dispensing module 250 arranged in series along the machine direction 46. The first dispensing module 248 of this embodiment includes a first dispensing nozzle 242 that is a SureWrap® nozzle commercially available from Nordson Corporation of Westlake, Ohio, which is described in U.S. Pat. No. 7,578,882 to Harris et al., the entire disclosure of which is hereby incorporated by reference herein. The second dispensing module 250 of this embodiment includes a second dispensing nozzle such as the Universal™ CF nozzle commercially available from Nordson Corporation of Westlake, Ohio.

More particularly, and as described in further detail in U.S. Pat. No. 7,578,882 to Harris, the first dispensing nozzle 242 applies a first quantity 256 of adhesive formed by a filament impacted by a plurality of air jets to each elastic strand 28. The elastic strands 28 move faster than the first quantity 256 of adhesive, which causes the quantity 256 to stretch out during application onto the strands 28. As shown in FIGS. 5 and 6, this stretching of the first quantity 256 tends to separate or break the adhesive 30 into discrete localized increased masses 74 on the strands 28 that are separated from one another by thinner areas 76 of adhesive 30 running between adjacent masses 74. It will be understood that the thinner areas 76 may also break between adjacent increased masses 74, leaving no adhesive 30 between adjacent masses 74. Each of these discrete masses 74 of adhesive becomes a discrete bond point when the elastic strands 28 are adhered to the substrate 18. The second dispensing nozzle 244 applies a second quantity 258 of adhesive, which is a swirled filament of adhesive 30, onto all of the elastic strands 28 collectively. Thus, unlike the previous embodiment, the first dispensing nozzle 242 applies adhesive individually onto each elastic strand 28, while the second dispensing nozzle 244 applies adhesive collectively onto all of the elastic strands 28.

As shown in FIGS. 5 and 6, the first and second dispensing modules 248, 250 receive adhesive material from corresponding adhesive supplies 252, 254. Similar to the embodiments described above, the adhesive supplies 252, 254 may include separate individually adjustable pumps for each dispensing module 248, 250 or a shared dual stream pump for both dispensing modules 248, 250. Similar to the previous embodiment, the first dispensing nozzle 242 dispenses the first quantity 256 onto the first and third portions 32, 36 of the elastic strands 28, while the second dispensing nozzle 244 dispenses the second quantity 258 onto the second portions 34 of the elastic strands 28 only. Thus, as shown by the adhesive patterns shown in FIGS. 5 and 6, the first and third portions 32, 36 are coated with first and third volumes of adhesive 30a, 30c that are larger than a second volume of adhesive 30b coating the second portions 34. As with the previously described embodiment, the dispensing apparatus 240 advantageously applies a higher volume of adhesive 30 to the end portions 32, 36 of the elastic strands 28 than to the central portions 34, thereby significantly reducing adhesive use while maintaining similar high bond quality.

With reference to FIG. 7, yet another embodiment of a dispensing apparatus 340 for applying varying volumes of adhesive along the length of elastic strands 28 in accordance with the invention is shown. Similar to the previous embodiment, the dispensing apparatus 340 shown in FIG. 7 includes a first dispensing module 348 and a second dispensing module 350 arranged in series along the machine direction 46. The first dispensing module 348 of this embodiment includes a SureWrap® nozzle commercially available from Nordson Corporation of Westlake, Ohio, which is described in U.S. Pat. No. 7,578,882 to Harris et al. The second dispensing module 350 of this embodiment includes a non-contact swirl nozzle such as the Summitt™ Mini Swirl nozzle commercially available from Nordson Corporation of Westlake, Ohio, which is described in U.S. Pat. No. 4,815,660 to Boger.

More particularly, and as described in further detail in U.S. Pat. No. 7,578,882 to Harris, the first dispensing module 348 applies a first quantity 356 of adhesive formed by a filament impacted by a plurality of air jets to each elastic strand 28. The elastic strands 28 move faster than the first quantity 356 of adhesive, which causes the first quantity 356 to stretch out during application into discrete localized increased masses 74 on the strands 28 that are separated from one another by thinner (or broken) areas 76 of adhesive 30 running between adjacent masses 74. The second dispensing module 350 applies a second quantity 358 of adhesive, which is a miniature swirled filament of adhesive 30, onto each elastic strand 28 individually. Thus, unlike the previous embodiment, each of the first and second dispensing modules 348, 350 in this embodiment apply adhesive 30 individually onto each elastic strand 28.

As shown in FIG. 7, the first and second dispensing modules 348, 350 receive adhesive material from corresponding adhesive supplies 352, 354. Similar to the embodiments described above, the adhesive supplies 352, 354 may include separate individually adjustable pumps for each dispensing module 348, 350 or a shared dual stream pump for both dispensing modules 348, 350. Similar to the previous embodiment, the first dispensing module 348 dispenses the first quantity 356 onto the first and third portions 32, 36 of the elastic strands 28, while the second dispensing module 350 dispenses the second quantity 358 onto the second portions 34 of the elastic strands 28 only. Thus, as shown by the adhesive patterns shown in FIG. 7, the first and third portions 32, 36 are coated with first and third volumes of adhesive 30a, 30c that are larger than a second volume of adhesive 30b coating the second portions 34. As with the previously described embodiment, the dispensing apparatus 340 advantageously applies a higher volume of adhesive 30 to the end portions 32, 36 of the elastic strands 28 than to the central portions 34, thereby significantly reducing adhesive use while maintaining similar high bond quality.

Figure 8:
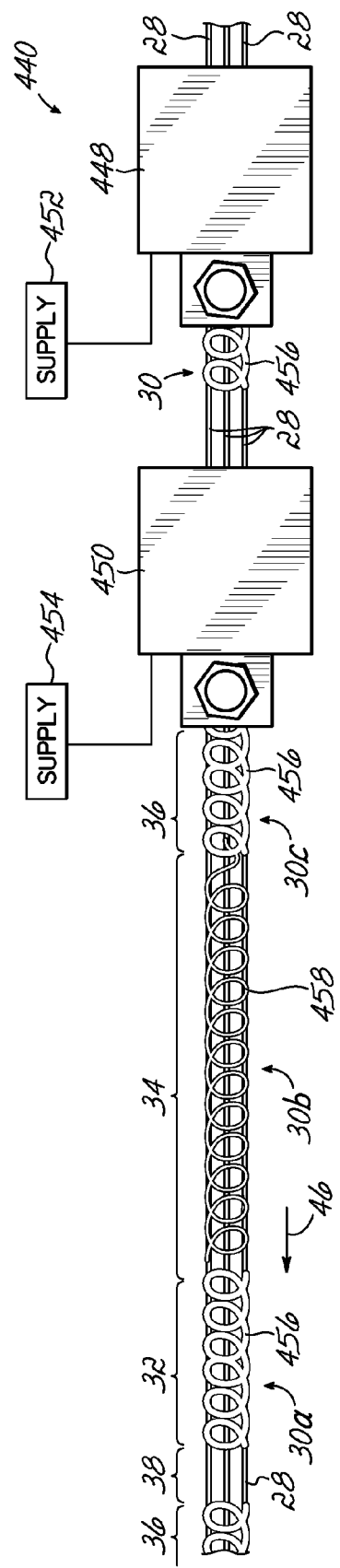
FIG. 8 is a schematic top view of another embodiment of a dispensing apparatus for applying adhesive to elastic strands.

With reference to FIG. 8, another embodiment of a dispensing apparatus 440 for applying varying volumes of adhesive along the length of elastic strands 28 in accordance with the invention is shown. Similar to the previous embodiment, the dispensing apparatus 440 shown in FIG. 8 includes a first dispensing module 448 and a second dispensing module 450 arranged in series along the machine direction 46. The first dispensing module 448 of this embodiment includes a non-contact swirl nozzle such as the Universal™ CF nozzle commercially available from Nordson Corporation of Westlake, Ohio. The second dispensing module 450 of this embodiment also includes a non-contact swirl nozzle such as the Universal™ CF nozzle commercially available from Nordson Corporation of Westlake, Ohio.

More particularly, the first dispensing module 448 applies a first quantity 456 of adhesive which is formed by a filament swirled by air jets onto all of the elastic strands 28 collectively. Similarly, the second dispensing module 450 applies a second quantity 458 of adhesive which is formed by a filament swirled by air jets onto all of the elastic strands 28 collectively. Thus, unlike the previous embodiment, each of the first and second dispensing modules 448, 450 in this embodiment apply adhesive 30 collectively onto all of the elastic strands 28.

As shown in FIG. 8, the first and second dispensing modules 448, 450 receive adhesive material from corresponding adhesive supplies 452, 454. Similar to the embodiments described above, the adhesive supplies 452, 454 may include separate individually adjustable pumps for each dispensing module 448, 450 or a shared dual stream pump for both dispensing modules 448, 450. Similar to the previous embodiment, the first dispensing module 448 dispenses the first quantity 456 onto the first and third portions 32, 36 of the elastic strands 28, while the second dispensing module 450 dispenses the second quantity 458 onto the second portions 34 of the elastic strands 28. Thus, as shown by the thicker and thinner adhesive patterns shown in FIG. 8, the first and third portions 32, 36 are coated with first and third volumes of adhesive 30a, 30c that are larger than a second volume of adhesive 30*b* coating the second portions 34. As with the previously described embodiment, the dispensing apparatus 440 advantageously applies a higher volume of adhesive 30 to the end portions 32, 36 of the elastic strands 28 than to the central portions 34, thereby significantly reducing adhesive use while maintaining similar high bond quality.

With reference to FIG. 9, yet another embodiment of a dispensing apparatus 540 for applying varying volumes of adhesive along the length of elastic strands 28 in accordance with the invention is shown. Similar to the previous embodiment, the dispensing apparatus 540 shown in FIG. 9 includes a first dispensing module 548 and a second dispensing module 550 arranged in series along the machine direction 46. The first dispensing module 548 of this embodiment includes a non-contact swirl nozzle such as the Summitt™ Mini Swirl nozzle commercially available from Nordson Corporation of Westlake, Ohio. The second dispensing module 550 of this embodiment includes a non-contact swirl nozzle such as the Universal™ CF nozzle commercially available from Nordson Corporation of Westlake, Ohio.

More particularly, the first dispensing module 548 applies a first quantity 556 of adhesive, which is a miniature swirled filament of adhesive 30, onto each elastic strand 28 individually. The second dispensing module 550 applies a second quantity 558 of adhesive, which is formed by a filament swirled by air jets onto all of the elastic strands 28 collectively. Thus, unlike the previous embodiment, the first dispensing module 548 applies adhesive collectively onto all of the elastic strands 28, while the second dispensing module 550 applies adhesive individually onto each elastic strand 28.

As shown in FIG. 9, the first and second dispensing modules 548, 550 receive adhesive material from corresponding adhesive supplies 552, 554. Similar to the embodiments described above, the adhesive supplies 552, 554 may include separate individually adjustable pumps for each dispensing module 548, 550 or a shared dual stream pump for both dispensing modules 548, 550. Similar to the previous embodiment, the first dispensing module 548 dispenses the first quantity 556 onto the first and third portions 32, 36 of the elastic strands 28, while the second dispensing module 550 dispenses the second quantity 558 onto the second portions 34 of the elastic strands 28. Thus, as shown by the adhesive patterns shown in FIG. 9, the first and third portions 32, 36 are coated with first and third volumes of adhesive 30*a*, 30*c* that are larger than a second volume of adhesive 30*b* coating the second portions 34. As with the previously described embodiment, the dispensing apparatus 540 advantageously applies a higher volume of adhesive 30 to the end portions 32, 36 of the elastic strands 28 than to the central portions 34, thereby significantly reducing adhesive use while maintaining similar high bond quality.

With reference to FIG. 10, another embodiment of a dispensing apparatus 570 for applying varying volumes of adhesive along the length of elastic strands 28 in accordance with the invention is shown. Similar to the previous embodiment, the dispensing apparatus 570 shown in FIG. 10 includes a first dispensing module 578 and a second dispensing module 580 arranged in series along the machine direction 46. The first dispensing module 578 of this embodiment includes a non-contact swirl nozzle such as the Summitt™ Mini Swirl nozzle commercially available from Nordson Corporation of Westlake, Ohio. The second dispensing module 580 of this embodiment also includes a non-contact swirl nozzle such as the Summitt™ Mini Swirl nozzle commercially available from Nordson Corporation of Westlake, Ohio.

More particularly, the first dispensing module 578 applies a first quantity 586 of adhesive, which is a miniature swirled filament of adhesive 30, onto each elastic strand 28 individually. The second dispensing module 580 applies a second quantity 588 of adhesive, which is a miniature swirled filament of adhesive 30, onto each elastic strand 28 individually. Thus, unlike the previous embodiment, each of the first dispensing module 578 and the second dispensing module 580 applies adhesive individually onto each elastic strand 28.

As shown in FIG. 10, the first and second dispensing modules 578, 580 receive adhesive material from corresponding adhesive supplies 582, 584. Similar to the embodiments described above, the adhesive supplies 582, 584 may include separate individually adjustable pumps for each dispensing module 578, 580 or a shared dual stream pump for both dispensing modules 578, 580. Similar to the previous embodiment, the first dispensing module 578 dispenses the first quantity 586 onto the first and third portions 32, 36 of the elastic strands 28, while the second dispensing module 580 dispenses the second quantity 588 onto the second portions 34 of the elastic strands 28. Thus, as shown by the adhesive patterns shown in FIG. 10, the first and third portions 32, 36 are coated with first and third volumes of adhesive 30*a*, 30*c* that are larger than a second volume of adhesive 30*b* coating the second portions 34. As with the previously described embodiment, the dispensing apparatus 570 advantageously applies a higher volume of adhesive 30 to the end portions 32, 36 of the elastic strands 28 than to the central portions 34, thereby significantly reducing adhesive use while maintaining similar high bond quality.

FIGS. 11 and 12A show another embodiment of a dispensing apparatus 640 according to the invention. In this dispensing apparatus 640, a first dispensing module 648 and a second dispensing module 650 are arranged generally in parallel along the machine direction 46 defined by the movement of the elastic strands 28. The first and second dispensing modules 648, 650 include corresponding first and second dispensing nozzles 642, 644 that are non-contact swirl nozzles such as the Universal™ CF nozzle commercially available from Nordson Corporation of Westlake, Ohio. Thus, the first and second dispensing nozzles 642, 644 apply respective first and second quantities 656, 658 of adhesive simultaneously onto the first portion 32 and then the third portion 36 of the plurality of elastic strands 28. In contrast to previous embodiments, the first dispensing nozzle 642 dispenses the first quantity 656 onto the first and third portions 32, 36 of the strands 28, while the second dispensing nozzle 644 dispenses the second quantity 658 onto the first, second, and third portions 32, 34, 36. Thus, as shown schematically by the overlaid spiral patterns in FIG. 11, the first and third portions 32, 36 are coated with first and third volumes of adhesive 30*a*, 30*c*, respectively, that are larger than a second volume of adhesive 30*b* coating the second portion 34. It will be understood that any of the embodiments of the dispensing apparatus shown herein may dispense overlapping quantities of adhesive 30 onto the first and third portions 32, 36 as shown in FIGS. 11 and 12A, or may dispense a completely separate first quantity on the first and third portions 32, 36 and a second quantity on the second portions 34 as shown in FIGS. 2 through 10.

Similar to the previous embodiment, the first dispensing nozzle 642 receives adhesive material pumped from a first adhesive supply 652 and the second dispensing nozzle 644 receives adhesive material pumped from a second adhesive supply 654. As described above, these first and second adhesive supplies 652, 654 may be separate individually adjustable pumps or may be the two output streams of a single dual stream pump. It will be understood that the first and second dispensing nozzles 642, 644 may be the same type of dispensing nozzle or different types of dispensing nozzles in various embodiments in accordance with the invention.

The simultaneous dispensing of the first and second quantities 656, 658 of adhesive is schematically shown from a front view in FIG. 12A. Each of the first and second dispensing nozzles 642, 644 may include corresponding first and second adhesive outlets 680, 682 that are angled slightly towards one another. As a result, the first and second quantities 656, 658 may entangle together slightly as they swirl towards the plurality of elastic strands 28. However, it will be appreciated that such entanglement of the quantities 656, 658 is only schematically shown in FIG. 12A and may be less complex than illustrated. As with the previously described embodiment, the dispensing apparatus 640 advantageously applies more volume of adhesive to the end portions 32, 36 of the elastic strands 28 than to the central portion 34, thereby significantly reducing adhesive use while maintaining similar high bond quality.

It will be understood that while the first and second dispensing modules 648, 650 and the first and second adhesive outlets 680, 682 are shown as directly parallel along the machine direction 46 in FIGS. 11 and 12A, another slightly modified embodiment of the dispensing apparatus 740 may include slightly offset elements along the machine direction 46. As shown in FIG. 12B, this dispensing apparatus 740 again includes first and second dispensing modules 748, 750 having first and second dispensing nozzles 742, 744 with first and second adhesive outlets 780, 782. The first dispensing module 748 is slightly offset forwards from the second dispensing module 750, which reduces or eliminates the entanglement of first and second filaments 756, 758 of adhesive during flight to the elastic strands 28. In all other respects, the dispensing apparatus 740 of FIG. 12B operates in an identical manner as the dispensing apparatus 640 of FIGS. 11 and 12A, and thus no further explanation is provided here.

Although the previous embodiments of the dispensing apparatus have included two separate dispensing modules and dispensing nozzles, it will be understood that the same method of applying more adhesive at the end portions 32, 34 of elastic strands 28 may be performed by a single dispensing module connected to an adjustable supply of adhesive 30 or multiple supplies of adhesive 30. In this regard, FIGS. 13-17 illustrate various embodiments of a dispensing apparatus 840, 940, 1040 that only include a single dispensing module and a single dispensing nozzle. These single module embodiments may include various types of dispensing nozzles, as described in further detail below.

With reference to FIG. 13, another embodiment of a dispensing apparatus 840 for applying varying volumes of adhesive along the length of elastic strands 28 in accordance with the invention is shown. Unlike previous embodiments, the dispensing apparatus 840 shown in FIG. 13 includes only a single dispensing module 848. The dispensing module 848 of this embodiment includes a contact dispensing nozzle 842 as described in U.S. Patent Application No. 61/474,129 to Saine. More particularly, and as described in further detail in U.S. Patent Application No. 61/474,129 to Saine, the dispensing nozzle 842 applies a quantity 856, 858 of adhesive, which is a quantity applied by contacting the elastic strand 28 with an extruded adhesive 30 and then blowing air onto the elastic strand 28 to spread the adhesive 30 around the elastic strand 28. Thus, in this embodiment, the dispensing nozzle 842 applies adhesive 30 individually onto each elastic strand 28. The quantity 856, 858 includes a first adhesive portion 856 that is thicker or includes more adhesive 30 than a second adhesive portion 858, as described in further detail below.

In order to apply these adhesive portions 856, 858 with different amounts of adhesive 30, the dispensing module 848 receives adhesive from two adhesive supplies 852, 854. Similar to the embodiments described above, the adhesive supplies 852, 854 may include separate individually adjustable pumps or a shared dual stream pump, depending on the particular application. The dispensing module 848 includes first and second valves 890, 892 configured to control whether a dispensing outlet 880 of the dispensing nozzle 842 receives adhesive from one, both, or neither of the adhesive supplies 852, 854. One alternative arrangement of the first and second valves 890, 892 is shown in FIG. 14, and another arrangement of the first and second valves 890*a*, 892*a* is shown in FIG. 15. It will be understood that the particular arrangement of the valves 890, 892 and how the module 848 actuates those valves 890, 892 may be modified in other manners without departing from the scope of the invention. For example, the module 848 may include a single source of actuation for both valves 890, 892 or independent sources of actuation, and the adhesive passages 894, 896 described below may not be angled relative to one another when a single source of actuation is used.

Turning to the arrangement shown in FIG. 14, the first valve 890 is positioned in a first angled passage 894 that receives adhesive 30 from the first adhesive supply 852. The second valve 892 is positioned in a second angled passage 896 receiving adhesive 30 from the second adhesive supply 854. Each of the first and second angled passages 894, 896 terminates in close proximity to the dispensing outlet 880, which is advantageous because this arrangement limits the passage space between the shutoff valves 890, 892 and the dispensing outlet 880 (to this end, flow of adhesive 30 is terminated proximate to the dispensing outlet 880 whenever one of the valves 890, 892 is closed). Thus, the amount of adhesive 30 that may drip or leak out of the dispensing nozzle 842 after the valves 890, 892 are closed is minimized. Additionally, the first and second valves 890, 892 are arranged in parallel within the dispensing module 848 such that each valve 890, 892 independently controls the on/off supply of adhesive 30 from the corresponding adhesive supplies 852, 854. This parallel arrangement of valves 890, 892 is similar to that arrangement which is described in U.S. Pat. No. 7,152,815 to Harris et al., the entire disclosure of which is hereby incorporated by reference herein. To this end, when both of the valves 890, 892 are open, a maximum flow of adhesive 30 is extruded through the dispensing outlet 880. When only one of the valves 890, 892 is open with the other closed, a lesser flow of adhesive 30 is extruded through the dispensing outlet 880. Thus, by controlling the operation of the valves 890, 892, the relative thickness of the coating formed by the quantity 856, 858 may be modified.

More particularly, the dispensing module 848 opens both valves 890, 892 to apply a thicker first adhesive portion 856 at the first and third portions 32, 36 of the elastic strands 28. The dispensing module 848 then closes one of the valves 890, 892 to apply a thinner second adhesive portion 858 at the second portion 34 of the elastic strands 28. When both valves 890, 892 are closed, substantially no adhesive 30 is extruded onto the elastic strands 28, such as for example at the free ends 38. Thus, as shown by the adhesive patterns shown in FIG. 13, the first and third portions 32, 36 are coated with first and third volumes of adhesive 30a, 30c that are larger than a second volume of adhesive 30b coating the second portions 34. As with the previously described embodiment, the dispensing apparatus 840 advantageously applies a higher volume of adhesive 30 to the end portions 32, 36 of the elastic strands 28 than to the central portions 34, thereby significantly reducing adhesive use while maintaining similar high bond quality.

In an alternative operation of the dispensing module 848 and valves 890, 892 shown in FIG. 14, the different flows or "volumes" of adhesive 30 are provided by selectively opening only one of the valves 890, 892 at a time. In such an arrangement, the separate individually adjustable pumps defining the first and second adhesive supplies 852, 854 are controlled to provide different (adjustable) amounts of flow of adhesive 30 into the first and second angled passages 894, 896. For example, the first adhesive supply 852 may be configured to deliver sufficient flow of adhesive 30 to produce a volume of 0.2 g/m on the elastic strands 28, while the second adhesive supply 854 may be configured to deliver sufficient flow of adhesive 30 to produce a volume of 0.1 g/m on the elastic strands 28. It will be understood that the exact volumes may be modified in other embodiments. As a result of these different amounts of flow, the dispensing module 848 achieves varying volumes by alternatively opening either the first valve 890 or the second valve 892. To this end, the dispensing module 848 opens the first valve 890 and closes the second valve 892 to apply a thicker first adhesive portion 856 at the first and third portions 32, 36 of the elastic strands. In between the first and third portions 32, 36, the dispensing module 848 closes the first valve 890 and opens the second valve 892 to apply a thinner second adhesive portion 858 at the second portion 34 of the elastic strands 28. When both valves 890, 892 are closed, substantially no adhesive 30 is extruded onto the elastic strands 28, such as for example at the free ends 38. In such an embodiment or operation, the valves 890, 892 are not configured to be opened at the same time, as the difference in volume output is provided by controlling the first and second adhesive supplies 852, 854 as described above.

It will be understood that the opening of the first valve 890 and/or the second valve 892 may be done in a continuous or intermittent manner during dispensing adhesive 30 onto the elastic strands 28. For example, the second portion 34 of the elastic strands 28 may be coated with the second adhesive portion 858 by keeping the first valve 890 closed and repeatedly opening and closing the second valve 892 to provide generally spaced-apart masses of adhesive 30 along the length of the second portion 34. Alternatively, the second portion 34 of the elastic strands 28 may be coated with the second adhesive portion 858 by keeping the second valve 892 continuously open while the first valve 890 is closed, which produces a generally uniform coating of adhesive 30 along the length of the second portion 34. It will be appreciated that the flow rate of adhesive 30 delivered by the individually adjustable pump defining the second adhesive supply 854 will be larger when the second valve 892 is to be opened intermittently than when the second valve 892 is to be opened continuously in order to provide the same level of adhesive coating on the second portion 34 of the elastic strands 28. Moreover, it will be understood that the application of adhesive 30 onto the first and third portions 32, 36 may be similarly adjusted by opening the first valve 890 intermittently or continuously in other embodiments.

Thus, just as in the previous exemplary operation, the first and third portions 32, 36 of the elastic strands 28 are coated with first and third volumes of adhesive 30a, 30c that are larger than a second volume of adhesive 30b coating the second portions 34 of the elastic strands 28. The application of a higher volume of adhesive 30 to the end portions 32, 36 of the elastic strands 28 than to the central portions 34 maintains high quality bonds capable of preventing creep at the opposing ends of the elastic strands 28 (defined by the end portions 32, 36) when adhesively secured to the substrate(s) 18, 26 to form the elasticized leg gather 20 on the disposable diaper 10. In other words, the integrity of the bonds formed between the elastic strands 28 and the substrate(s) 18, 26 is maintained by the first and third volume of adhesive 30a, 30c during normal wear conditions for the disposable diaper 10, and these bonds limit movement of the opposing ends of the elastic strands 28. Also, the reduced use of adhesive along the second portions 34 enables increased softness and force retraction capability for the disposable diaper 10 at least along these portions, compared to conventional designs. In this regard, the stiffness of the disposable diaper 10 is limited or reduced and the elastic strands 28 are allowed to retract from the stretched condition along the second portions 34.

Turning to FIG. 15, an alternative arrangement of the first and second valves 890a, 892a is shown. In this embodiment, the first valve 890a and the second valve 892a are arranged in series within the dispensing module 848. To this end, the first valve 890a is positioned in a first passage 894a that receives adhesive 30 from the first adhesive supply 852. The second valve 892a is positioned in a second passage 896a receiving adhesive 30 from the second adhesive supply 854. Contrary to the previous valve arrangement, the first passage 894a terminates into the second passage 896a just upstream of the second valve 892a. Thus, the second valve 892a operates to control on/off flow of both adhesive supplies 852, 854 into the dispensing outlet 880 simultaneously, while the first valve 890a only controls whether the flow past the second valve 892a originates from one or two adhesive supplies 852, 854.

In operation, opening both valves 890a, 892a again causes a maximum flow of adhesive 30 to be extruded through the dispensing outlet 880. When only the second valve 892a is open with the first valve 890a closed, a lesser flow of adhesive 30 is extruded through the dispensing outlet 880. When the second valve 892a is closed, substantially no adhesive 30 is extruded through the dispensing outlet 880 from either adhesive supply 852, 854. Consequently, the valve arrangement shown in FIG. 15 is operable to produce the same advantageous pattern of adhesive on the elastic strands 28 as described in regard to FIGS. 13 and 14.

Figure 16:
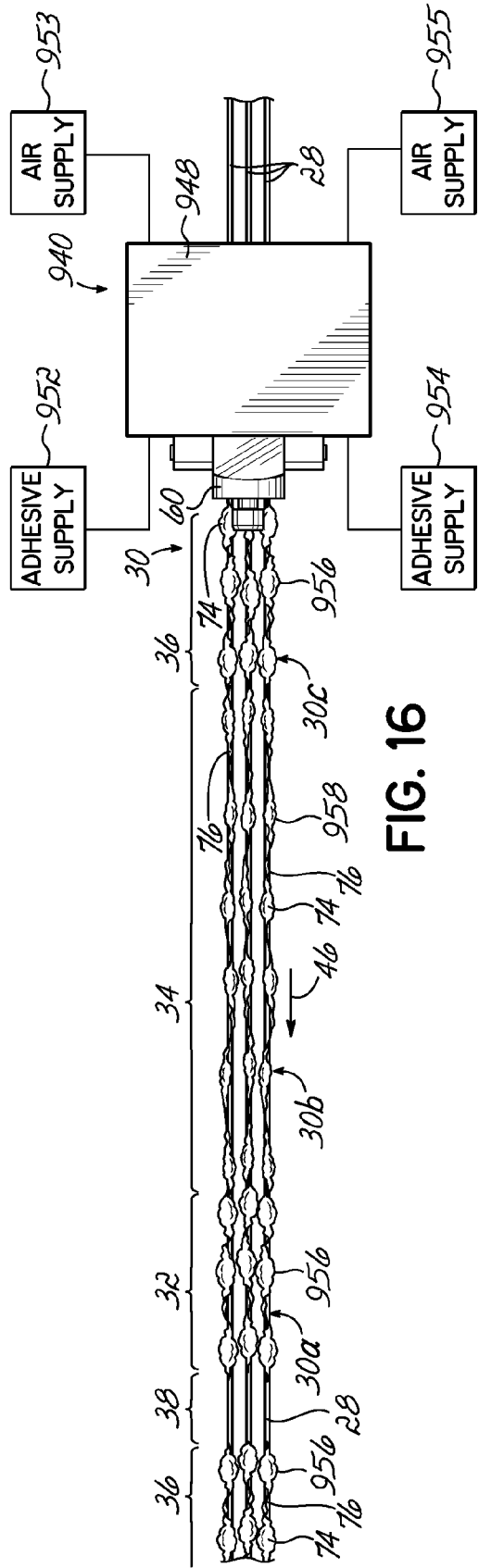
FIG. 16 is a schematic top view of another embodiment of a dispensing apparatus for applying adhesive to elastic strands.

With reference to FIG. 16, another embodiment of a dispensing apparatus 940 for applying varying volumes of adhesive along the length of elastic strands 28 in accordance with the invention is shown. As in the previous embodiment, the dispensing apparatus 940 shown in FIG. 16 includes only a single dispensing module 948. The dispensing module 948 of this embodiment includes a SureWrap® nozzle commercially available from Nordson Corporation of Westlake, Ohio. More particularly, the dispensing nozzle applies a quantity 956, 958 of adhesive formed by a filament impacted by a plurality of air jets to each elastic strand 28. The elastic strands 28 move faster than the quantity 956, 958 of adhesive, which causes the quantity 956, 958 to stretch out during application into discrete localized increased masses 74 on the strands 28 that are separated from one another by thinner (or broken) areas 76 of adhesive 30 running between adjacent masses 74. Thus, in this embodiment, the dispensing module 948 applies adhesive 30 individually onto each elastic strand 28. The quantity 956, 958 includes a first adhesive portion 956 that includes more adhesive 30 than a second adhesive portion 958, as indicated schematically by closer spaced masses 74 of adhesive 30 in the first adhesive portion 956.

In order to apply these adhesive portions 956, 958 with different amounts of adhesive 30, the dispensing module 948 receives adhesive from two adhesive supplies 952, 954. Similar to the embodiments described above, the adhesive supplies 952, 954 may include separate individually adjustable pumps or a shared dual stream pump, depending on the particular application. The dispensing module 948 includes first and second valves (not shown) configured to control whether a dispensing outlet (not shown) of the dispensing nozzle receives adhesive from one, both, or neither of the adhesive supplies 952, 954, as described above. Additionally, the dispensing module 948 also receives pressurized process air from two air supplies 953, 955. The pressurized air from these air supplies 953, 955 may be selectively controlled by similar valves as the adhesive 30, as well understood in the art. Accordingly, a higher amount of pressurized air may be used when a higher amount of adhesive 30 is being applied by the dispensing module 948. It will also be appreciated that the dispensing module 948 may receive a single adjustable pressurized air supply in other embodiments consistent with the scope of the invention. As with the previously described embodiments, the dispensing apparatus 940 advantageously applies more volume of adhesive to the end portions 32, 36 of the elastic strands 28 than to the central portion 34, thereby significantly reducing adhesive use while maintaining similar high bond quality.

Figure 17:
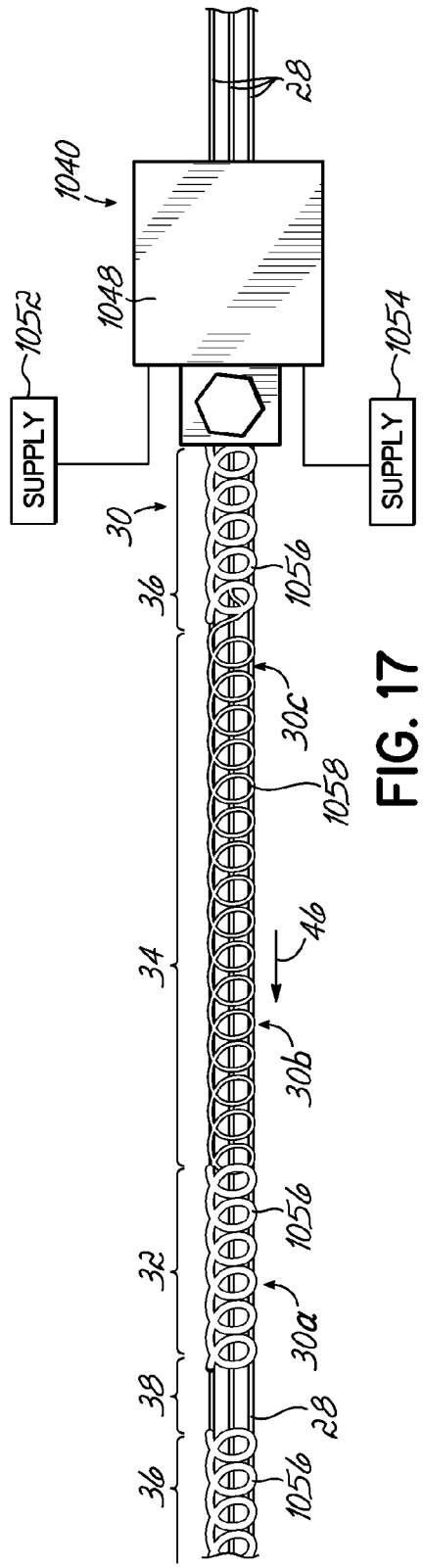
FIG. 17 is a schematic top view of yet another embodiment of a dispensing apparatus for applying adhesive to elastic strands.

With reference to FIG. 17, still another embodiment of a dispensing apparatus 1040 for applying varying volumes of adhesive along the length of elastic strands 28 in accordance with the invention is shown. As in the previous embodiment, the dispensing apparatus 1040 shown in FIG. 17 includes only a single dispensing module 1048. The dispensing module 1048 of this embodiment includes a Universal™ CF nozzle commercially available from Nordson Corporation of Westlake, Ohio. More particularly, the dispensing nozzle applies a quantity 1056, 1058 of adhesive formed by a swirled filament to all of the elastic strands 28 collectively. The quantity 1056, 1058 includes a first adhesive portion 1056 that includes more adhesive 30 than a second adhesive portion 1058, as indicated schematically by thicker and thinner swirl patterns shown in FIG. 17.

In order to apply these adhesive portions 1056, 1058 with different amounts of adhesive 30, the dispensing module 1048 receives adhesive from two adhesive supplies 1052, 1054. Similar to the embodiments described above, the adhesive supplies 1052, 1054 may include separate individually adjustable pumps or a shared dual stream pump, depending on the particular application. The dispensing module 1048 includes first and second valves (not shown) configured to control whether a dispensing outlet (not shown) of the dispensing nozzle receives adhesive from one, both, or neither of the adhesive supplies 1052, 1054, as described above. When both valves are open, the dispensing module 1048 applies the thicker first adhesive portion 1056 to the elastic strands 28. When only one of the valves is open, the dispensing module 1048 applies the thinner second adhesive portion 1058 to the elastic strands 28. As such, the dispensing apparatus 1040 advantageously applies more volume of adhesive to the end portions 32, 36 of the elastic strands 28 than to the central portion 34, thereby significantly reducing adhesive use while maintaining similar high bond quality.

Figure 18:
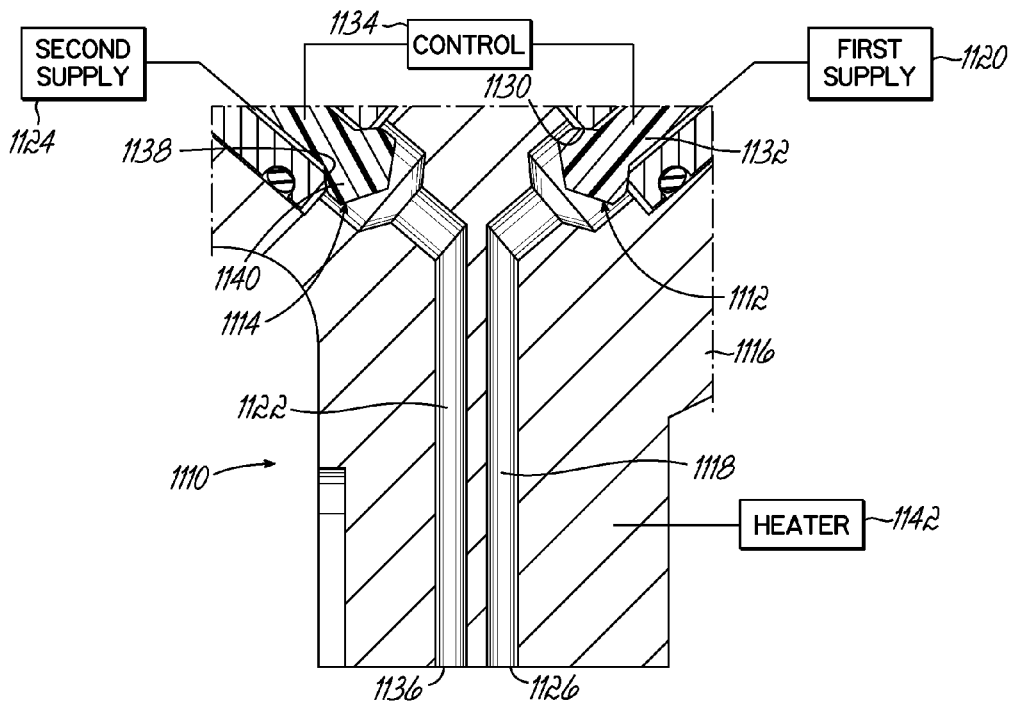
FIG. 18 is a cross-sectional side view of a module having separated flow passages for first and second adhesive streams, in accordance with another embodiment of a dispensing apparatus.

Another embodiment of a module 1110 configured for use in dispensing apparatus and methods using a single module 1110 and a single dispensing nozzle is shown in FIG. 18. As set forth in further detail below, the module 1110 maintains separation between adhesive streams all the way to the dispensing nozzle so as to avoid pressure differences in the adhesive streams generating an adverse effect on flow control elements like the first valve 1112 and the second valve 1114. As described above, it will be appreciated that the term "module" in the context of this embodiment as well as others refers generally to the applicator element(s) that supply and control flow of the adhesive streams into the nozzle, and it is well understood that such element(s) may take different forms depending on the user and the desired dispensing system and process. For example, the "module" may include one or more of: a manifold body, self-contained modules with flow control valves included, applicator bodies, and other known dispensing system components. The example shown in FIG. 18 includes valves (which may be part of modules as referred to in the art) that are plugged into receptacles formed in the manifold body (described as the "module body" 1116 below); however, such modules may instead be configured to mount on an outer face of the heated manifold body when the passages through the heated manifold body are reconfigured to enable control of flow at such outer face(s). In such embodiments, the manifold body receives the adhesive supplies and delivers adhesive streams into the nozzle based on the flow control provided at the valves in the modules, which are mounted in or on the heated manifold body. The example of this "module" set forth in detail below is only one example which has proven to be useful, but further modifications of the upstream applicator elements, collectively referred to as the "module" herein, are also to be considered within the scope of this invention.

With further reference to FIG. 18, the module 1110 of this embodiment includes a module body 1116 defining a first passage 1118 in communication with a first adhesive supply 1120 and a second passage 1122 in communication with a second adhesive supply 1124. The first passage 1118 terminates in a first module outlet 1126 that is configured to deliver a first adhesive stream from the first adhesive supply 1120 into the dispensing nozzle (not shown in FIG. 18), a couple further examples of which are provided below. The first passage 1118 also carries the first valve 1112 that controls flow of the first adhesive stream through the module 1110 and to the nozzle. To this end, the first valve 1112 includes a first valve seat 1130 defined in the first passage 1118 and a first valve member 1132 that can be moved by a control 1134 between open and closed positions relative to the first valve seat 1130, thereby selectively allowing or blocking flow of the first adhesive stream in the first passage 1118. The control 1134 is shown schematically in FIG. 18, but it will be readily understood that this can be any control computer or other similar device that actuates movements of valve members using appropriate actuators (mechanical, electrical, pneumatic, etc.). Thus, the control 1134 operates the first valve 1112 to provide the first adhesive stream from the module 1110 when desired for dispensing on an elastic strand.

In a similar manner as the first passage 1118, the second passage 1122 terminates in a second module outlet 1136 that is configured to deliver a second adhesive stream from the second adhesive supply 1124 into the dispensing nozzle (not shown in FIG. 18). The second passage 1122 also carries the second valve 1114 that controls flow of the second adhesive stream through the module 1110 and to the nozzle. To this end, the second valve 1114 includes a second valve seat 1138 defined in the second passage 1122 and a second valve member 1140 that can be moved by the control 1134 between open and closed positions relative to the second valve seat 1138, thereby selectively allowing or blocking flow of the second adhesive stream in the second passage 1122. Thus, the control 1134 operates the second valve 1114 to provide the second adhesive stream from the module 1110 when desired for dispensing on an elastic strand. It will also be understood that while one control 1134 is schematically shown, separate control devices can be associated with each of the first and second valves 1112, 1114 in other embodiments, but these separate control devices would still need to communicate and coordinate with one another to provide the desired dispensing patterns on an elastic strand.

The module body 1116 is designed so as to separate the flow paths for the first and second adhesive streams. In this regard, the first and second passages 1118, 1122 are separated within the module body 1116 and do no intersect at any point within the module 1110. This separation of the adhesive streams results in an independence from adverse effects on valve actuation that could otherwise be caused if the first and second passages 1118, 1122 intersected one another within the module 1110, particularly if the intersection was positioned immediately downstream from the first and second valves 1112, 1114. For example, if the first adhesive stream is delivered into the module 1110 at a greater flow rate and pressure than the second adhesive stream, then these differing pressures would result in a net force being applied to at least one of the first and second valve members 1132, 1140 opposing an opening or closing movement thereof (which can be referred to as a "back pressure"), which could modify in somewhat unpredictable manners the response time of valve member operation compared to signals from the control 1134. In this regard, testing has revealed that the first and second valves 1112, 1114 when using this embodiment of the module 1110 respond to control signals in a substantially identical manner as valves in a single flow path, single outlet module/nozzle arrangement of various conventional dispensing apparatus. Thus, by keeping the first and second passages 1118, 1122 and the corresponding first and second adhesive streams separated in the module 1110, these potentially adverse effects on valve/module actuation (including one or both valves opening or closing at a modified rate different than expected/designed) are effectively eliminated.

The module body 1116 is typically formed from a metallic material to enhance heat transfer from a heater 1142, shown schematically, into the adhesive streams flowing through the module 1110 in first and second passages 1118, 1122. It will be understood that the heater 1142 can include any known form of heating element or device, and one of more of such devices can be located in a manifold containing the module 1110, the module 1110 itself, and/or the nozzle in various embodiments consistent with this disclosure. Regardless of the specific arrangement, the heater 1142 is set to a temperature point so that heat transferred into both of the first and second adhesive streams results in an application temperature (at the nozzles described above and below) within the desired operating range of the adhesive material(s). Thus, in embodiments where the type of adhesive received from the first and second adhesive supplies 1120, 1124 is different (explained further below), typically the adhesive with the higher viscosity will dictate what the temperature set point of the heater 1142 needs to be to heat the module 1110 accordingly. Of course, when the same type of adhesive material is provided from both the first and second adhesive supplies 1120, 1124, at the same or differing pressures and flow rates, the heater 1142 will be set according to the desired application temperature operating range for that adhesive material.

Figure 19:
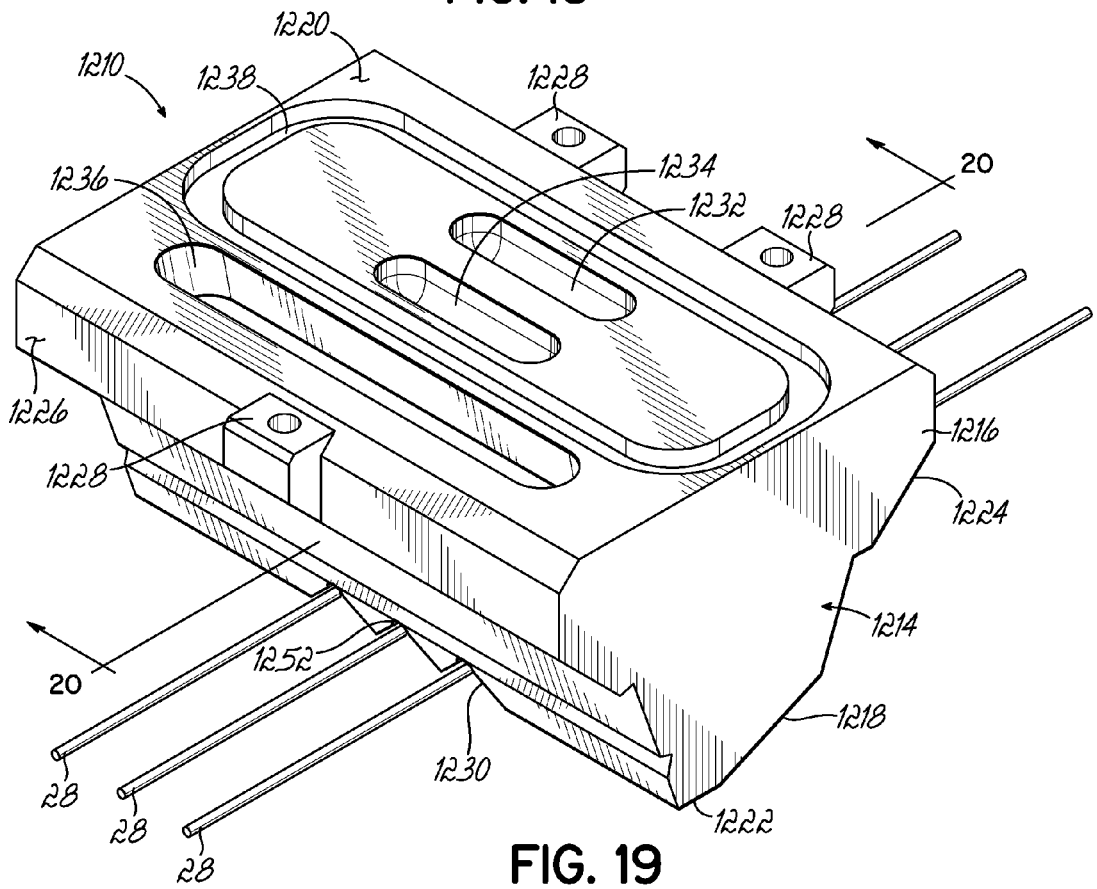
FIG. 19 is a top perspective view of one embodiment of a contact dispensing nozzle including separated nozzle inlets configured to be used with the module of FIG. 18 in a dispensing apparatus.
Figure 20:
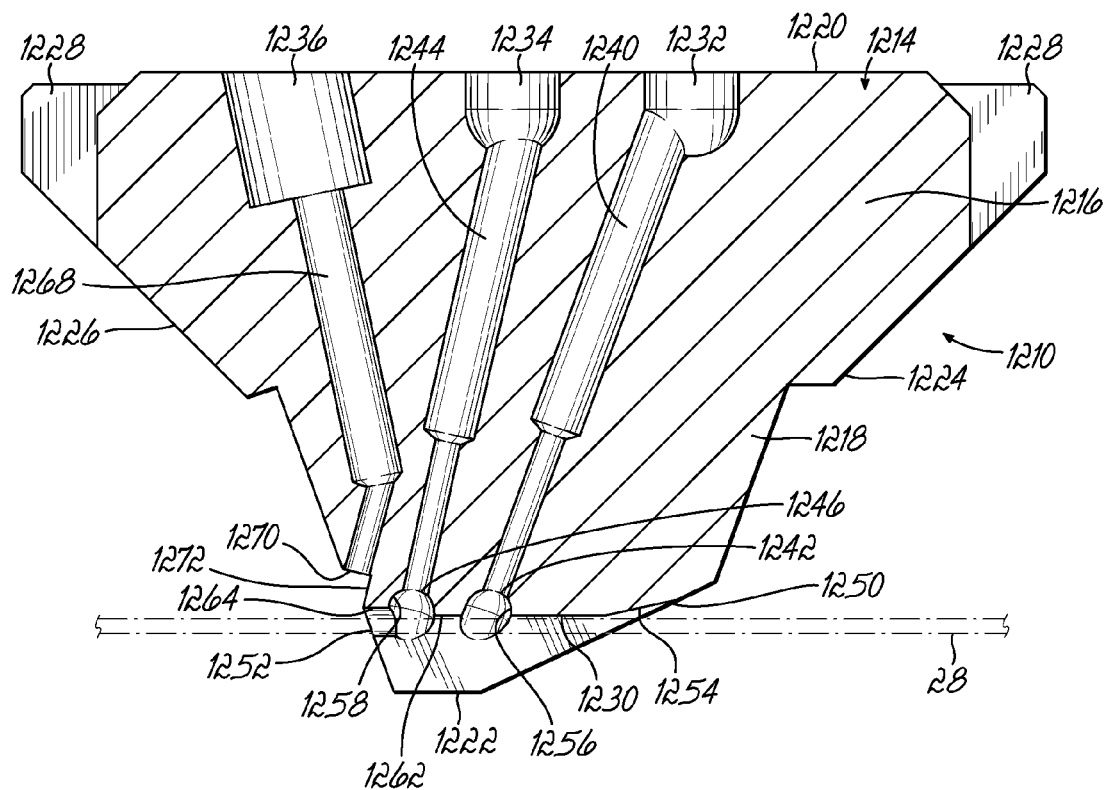
FIG. 20 is a cross-sectional side view of the dispensing nozzle of FIG. 19, taken along line 20-20 at the location of one of the slots acting as a strand guide, showing further details of internal adhesive and air flow passages within the nozzle.

As described above, the module 1110 shown in FIG. 18 is configured to deliver separated flows of first and second adhesive streams into a dispensing nozzle, and one such embodiment of a contact dispensing nozzle 1210 is illustrated in FIGS. 19 and 20. The nozzle 1210 is a modified version of the Allegro™ Elastic Attachment Nozzle commercially available from Nordson Corporation of Westlake, Ohio, several versions of which are described in U.S. Pat. No. 9,168,554 to Saine et al., initially referenced above. Although only one version of this modified embodiment of the nozzle 1210 is described in detail and shown in FIGS. 19 and 20, it will be understood that the additional features and modifications shown in the embodiments of the Saine '554 Patent beyond the so-called V-notch embodiment may also be included, if desired, without departing from the scope of this disclosure.

The nozzle 1210 is shown in perspective view in FIG. 19 and in side cross-section in FIG. 20 to clarify the internal and external features, particularly those that have been modified to make this nozzle 1210 operable with the module 1110 described above and with the corresponding embodiments of the dispensing apparatus and methods of this invention. To this end, the nozzle 1210 of this embodiment is configured to receive separated first and second adhesive streams and then apply them by contact dispensing onto one or more elastic strands, in such a manner that enables wet-on-wet contact dispensing of adhesive.

The nozzle 1210 includes a nozzle body 1214 having an upper body portion 1216 and a lower body portion 1218. The nozzle body 1214 also includes a top side 1220, a bottom side 1222, a front side 1224 extending between the top and bottom sides 1220, 1222, and a rear side 1226 extending between the top and bottom sides 1220, 1222. The top side 1220 defines a mounting surface configured to abut the module 1110 when the nozzle 1210 is coupled to the module 1110. The upper body portion 1216 is generally longer along the machine direction than the lower body portion 1218 from the front side 1224 to the rear side 1226, thereby giving the nozzle 1210 a tapered appearance from the top side 1220 to the bottom side 1222. Thus, the upper body portion 1216 in this embodiment defines connection portions 1228 along the front side 1224 and the rear side 1226 for aligning the nozzle 1210 with the module 1110. The nozzle 1210 is clamped to the module 1110 such that the top side 1220 is coupled to the module 1110 as well understood from U.S. Pat. Nos. 6,676,038 and 7,559,487.

In some embodiments, the nozzle body 1214 may have a different shape and size, including but not limited to being formed by stacked plates. Furthermore, although the nozzle 1210 is shown with three parallel elastic strands 28 running through separated slots 1230 at the bottom side 1222, only one of these elastic strands 28 and slots 1230 is shown with respect to the cross-section at FIG. 20 as each of these is arranged similarly within the nozzle 1210 (additionally, the total number of slots 1230 can be modified in other embodiments depending on the needs of the end user, e.g., how many elastic strands 28 are to be used for a hygiene product).

With reference to FIG. 19, the nozzle 1210 further includes a first nozzle inlet 1232, a second nozzle inlet 1234, and an air inlet 1236 disposed along the mounting surface at the top side 1220 of the nozzle body 1214. The first and second nozzle inlets 1232, 1234 are configured to receive adhesive streams from the module 1110, and are therefore surrounded by a seal groove 1238 that receives a seal member (not shown) to be placed between the nozzle 1210 and the previously-described module 1110. As shown in FIG. 20, the first nozzle inlet 1232 is coupled in fluid communication with a first adhesive passage 1240 that leads to a first nozzle outlet 1242 located at the bottom side 1222 of the nozzle 1210, specifically at the corresponding slot 1230. Likewise, the second nozzle inlet 1234 is coupled in fluid communication with a second adhesive passage 1244 that leads to a second nozzle outlet 1246 located at the bottom side 1222 of the nozzle 1210, specifically at the same slot 1230. The first adhesive passage 1240 and the second adhesive passage 1244 are both shown as generally straight bores which can be drilled into the nozzle body 1214 as well understood in the art, although the specific shape and layout of these adhesive passages 1240, 1244 could be modified in other similar embodiments.

Each of the first and second nozzle inlets 1232, 1234 may be fluidically coupled to a plurality of generally parallel first and second adhesive passages 1240, 1244 formed in the nozzle body 1214 and extending into the lower body portion 1218 thereof, with each set of first and second adhesive passages 1240, 1244 feeding outlets in one of the slots 1230 to thereby provide adhesive coating of the multiple elastic strands 28 as shown in FIG. 19. It will be understood that in embodiments with multiple slots 1230 and sets of first and second adhesive passages 1240, 1244, these first and second adhesive passages 1240, 1244 do not intersect one another within the nozzle body 1214, thereby advantageously maintaining the separation between first and second adhesive streams all the way to the point of dispensing from the first and second nozzle outlets 1242, 1246 onto the elastic strand(s) 28. As described further below, this arrangement enables wet-on-wet contact dispensing of adhesive onto elastic strands 28, which allows for varying volumes per unit length to be applied as well as different adhesive materials in the different portions of the elastic strands 28.

With continued reference to FIG. 20, further features of the slot 1230 and the nozzle body 1214 are shown, with the elastic strand 28 and the adhesive materials/streams not shown to reveal additional elements. To this end, the slot 1230 is generally formed as a V-shaped notch that extends from an inlet end 1250 located at the front side 1224 of the nozzle body 1214 to an outlet end 1252 located at the rear side 1226 of the nozzle body 1214. With the exception of several portions described below, the slot 1230 is formed by two converging surfaces extending away from one another towards the bottom side 1222 of the nozzle body 1214. As described in further detail below, the intersection of the slot 1230 with the rear side 1226 and air flow provided at the rear side 1226 collectively encourage release of adhesive material from the nozzle 1210. Adjacent the inlet end 1250, the slot 1230 is further defined by chamfered opening portions 1254 that broaden the size of the opening into the slot 1230, thereby reducing a likelihood of the elastic strand 28 running past and/or being caught upon a sharp edge at the nozzle body 1214. The slot 1230 therefore defines a strand guide portion for the nozzle 1210 and does not require a separate strand guide element in this embodiment (of course, such an element could be provided in alternative embodiments without departing from the scope of this disclosure).

At approximately halfway (or a little farther) along the length of the slot 1230, the slot 1230 is in fluid communication with the first adhesive passage 1240 via the first nozzle outlet 1242. As shown most clearly in FIG. 20, a first expansion chamber 1256 is formed in the nozzle body 1214, such as by using a ball-nose shaped mill in one example, to expand the size of the intersection between the slot 1230 and the first nozzle outlet 1242. The first expansion chamber 1256 includes a rounded profile in this embodiment and extends a small distance above a top edge of the slot 1230 such that the first nozzle outlet 1242 defines a substantially planar orifice for adhesive material to flow into the first expansion chamber 1256. As a result of the effects of die swell within the larger diameter first expansion chamber 1256, the adhesive will initially expand within the first expansion chamber 1256 and will be discharged from the first expansion chamber 1256 into contact with the elastic strand 28 in the slot 1230. The addition of the first expansion chamber 1256 enables the use of a smaller diameter first nozzle outlet 1242, such as 0.020 inches in the exemplary embodiment, which reduces the likelihood of adhesive material dripping out of the first nozzle outlet 1242 between dispensing cycles. In one example, the first expansion chamber 1256 defines a diameter of about 0.030 inches to about 0.070 inches.

Spaced apart from the first expansion chamber 1256 and in a downstream direction (relative to the machine direction of movement defined by the elastic strand 28), the slot 1230 is in fluid communication with the second adhesive passage 1244 via the second nozzle outlet 1246. To this end, the intersection of the slot 1230 and the second nozzle outlet 1246 is located closer to the outlet end 1252 than the inlet end 1250 in this embodiment. Similar to the first expansion chamber 1256 described above, a second expansion chamber 1258 is formed in the nozzle body 1214, such as by using a ball-nose shaped mill in one example, to expand the size of the intersection between the slot 1230 and the second nozzle outlet 1246. The second expansion chamber 1258 includes a rounded profile in this embodiment and extends a small distance above a top edge of the slot 1230 such that the second nozzle outlet 1246 defines a substantially planar orifice for adhesive material to flow into the second expansion chamber 1258 (these elements may have similar exemplary dimensions as those set forth above). As a result of the effects of die swell within the larger diameter second expansion chamber 1258, the adhesive will initially expand within the second expansion chamber 1258 and will be discharged from the second expansion chamber 1258 into contact with the elastic strand 28 in the slot 1230.

It will be understood that the first and second expansion chambers 1256, 1258 may be formed by other known cutting, drilling, and machining methods such as cutting scallop-shaped cutouts into the converging surfaces defining the slot 1230 in other embodiments to modify the shape or size of the first and second expansion chambers 1256, 1258 without departing from the scope of the current invention. It will also be appreciated that the diameter of the first and second nozzle outlets 1242, 1246 may be modified to adjust the velocity or flow of the adhesive exiting the first and second expansion chambers 1256, 1258 and spreading around the elastic strand 28 in other embodiments consistent with the current invention.

As shown in FIG. 20 (and also in larger views shown in FIGS. 21 through 22B), the slot 1230 also includes features which ensure that the adhesive that is contact dispensed onto the elastic strand 28 at the first and/or second expansion chambers 1256, 1258 remains on the elastic strand 28 during movement in the machine direction through the remainder of the slot 1230. To this end, the converging surfaces of the slot 1230 are configured to provide an initial wiping-type action to help spread some of the adhesive around a periphery of the elastic strand 28, but these surfaces should not strip the adhesive off of the rapidly-moving elastic strand 28. Accordingly, the slot 1230 includes a first groove 1262 extending between the first and second expansion chambers 1256, 1258 and a second groove 1264 extending between the second expansion chamber 1258 and the outlet end 1252 at the rear side 1226 of the nozzle 1210. Both of the first and second grooves 1262, 1264 are defined by extending a top of the slot 1230 farther upwardly into the nozzle body 1214, thereby providing more clearance for adhesive to be carried on the elastic strand 28 through the slot 1230. The second groove 1264 is larger in size than the first groove 1262, which is emphasized or exaggerated in the Figures for the sake of clarity, such that more adhesive can be carried by the elastic strand 28 downstream from the second expansion chamber 1258. Thus, regardless of whether the second adhesive stream provides a greater flow rate/volume of adhesive on portions of the elastic strand 28 than other portions receiving the first adhesive stream, or the first and second adhesive streams are combined on the elastic strand in some portions to form a greater volume of adhesive, this larger volume of adhesive is successfully carried through the slot 1230 at the larger second groove 1264 so as to remain on the elastic strand 28 upon exit from the nozzle 1210.

FIG. 20 also illustrates additional features of the path for pressurized air in the nozzle 1210. In this regard, the air inlet 1236 at the top side 1220 of the nozzle body 1214 is fluidically coupled to a plurality of air passages 1268 formed in the nozzle body 1214 and extending into the lower body portion 1218. In this embodiment, there is one air passage 1268 associated with each slot 1230 and elastic strand 28, so only one of the air passages 1268 is visible in the cross-section at FIG. 20. As with the first and second adhesive passages 1240, 1244, the air passage 1268 is drilled into the nozzle body 1214 at a location spaced apart from the first and second adhesive passages 1240, 1244 to avoid interference of air and adhesive stream flows. The air passage 1268 delivers air from the air inlet 1236 to an air outlet 1270 directed towards the adhesive in contact with the elastic strand 28 as the elastic strand 28 exits the outlet end 1252 of the corresponding slot 1230. More particularly, the air outlet 1270 is positioned adjacent to a rear surface 1272 that intersects the slot 1230 and defines part of the rear side 1226 of the nozzle body 1214. As such, air discharged from the air passage 1268 and the air outlet 1270 is directed along the rear surface 1272 to act on the adhesive as the strand 28 exits the slot 1230. The air outlet 1270 is specifically formed in an intermediate surface 1274 extending at an angle from the rear surface 1272. The thicknesses of the intermediate surface 1274 on opposite sides of the air outlet 1270 are minimized so as to reduce any eddy currents that would tend to form adjacent oblique surfaces surrounding the air outlet 1270. The reduction of eddy currents along the intermediate surface 1274 makes the delivery of air toward the elastic strand 28 more laminar.

Figure 21:
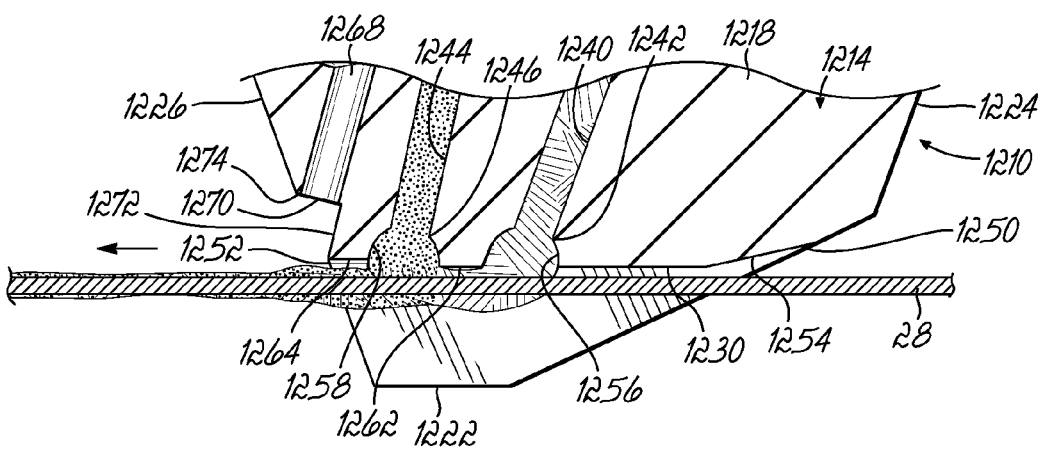
FIG. 21 is a partial cross-sectional side view of a lower portion of the dispensing nozzle similar to FIG. 20, illustrating an elastic strand moving through the slot with first and second adhesive streams being applied by contact dispensing to the elastic strand.
Figure 22A:
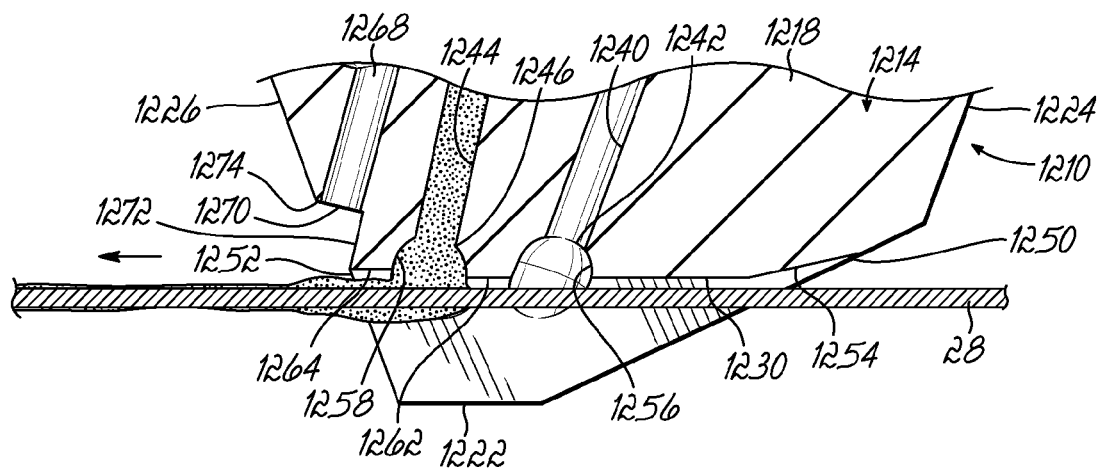
FIG. 22A is a partial cross-sectional side view similar to FIG. 21, but with only the second adhesive stream being applied by contact dispensing to the elastic strand.
Figure 22B:
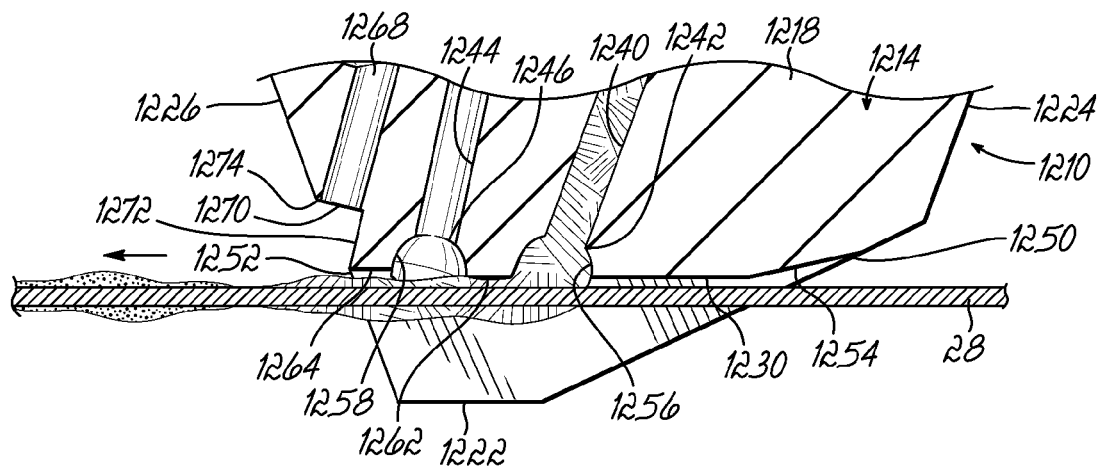
FIG. 22B is a partial cross-sectional side view similar to FIG. 22A, but with only the first adhesive stream being applied by contact dispensing to the elastic strand after the elastic strand has moved from the position shown in FIG. 22A.

Two exemplary operation examples for the nozzle 1210 are shown in FIG. 21 and in FIGS. 22A and 22B. Beginning with FIG. 21, the varying volumes of adhesive provided on different portions of the elastic strand 28 as set forth above (e.g., higher volumes on first and third portions that become opposing ends of the elastic strand 28 when adhered to the substrate(s), a lesser volume on the second portion in between the first and third portions of the elastic strand 28) are enabled by selectively contact dispensing both the first and second streams of adhesive onto the same portion of the elastic strand 28 as it moves through the slot 1230 of nozzle 1210. The first and second adhesive streams are shown with different cross-hatching for the sake of clarity in the illustration of these Figures. Thus, the elastic strand 28 first moves beneath the first expansion chamber 1256, where the first adhesive stream is being forced into contact with the elastic strand 28 (because the first valve 1112 in the module 1110 is controlled to the open position), then moves through the first groove 1262 and beneath the second expansion chamber 1258, where the second adhesive stream is being forced into contact with the elastic strand 28 (because the second valve 1114 in the module 1110 is also controlled to the open position). Having been coated with the first and second adhesive streams in wet-on-wet dispensing, this portion of the elastic strand 28 then moves through the second groove 1264 and the outlet end 1252 of the slot. At this point, the pressurized air from the air outlet 1270 is used to ensure release of adhesive from the rear side 1226 of the nozzle 1210 as well as to help spread the adhesive around the periphery of elastic strand 28.

To this end, upon release from the nozzle body 1214, the adhesive in contact with the elastic strand 28 is struck by pressurized air discharged from the air outlet 1270 toward the elastic strand 28. The pressurized air causes the adhesive, which is typically only partially spread around the periphery of the elastic strand 28 at the outlet end 1252 of the slot 1230, to spread more around the periphery of the elastic strand 28 in order to coat the elastic strand 28 with the adhesive. As alluded to above, it is believed that the mechanical movement of the adhesive with the converging surfaces defined by the slot 1230 immediately before this impact of the pressurized air further enhances the spreading effects caused by the pressurized air. The pressurized air discharged from the air outlet 1270 does not blow the adhesive off of the elastic strand 28 because the adhesive is applied in direct contact with the elastic strand 28 and begins forming an adhesive bond with the elastic strand 28 within the slot 1230. As a result, the adhesive coats substantially the entire periphery of the elastic strand 28 as is desired in hygiene product manufacturing. The pressurized air discharged from the air outlet 1270 along the rear surface 1272 also assists with release of adhesive from the nozzle body 1214 at the outlet end 1252. To this end, the adhesive remains attached to the moving elastic strand 28 downstream of the rear side 1226 rather than building up on the nozzle body 1214. As a result, the risk of adhesive building up, becoming charred, and blocking the air outlet 1270 is substantially reduced or eliminated.

Thus, when both the first and second valves 1112, 1114 of the module 1110 are opened as shown in FIG. 21, the first and second streams of adhesive can be combined on the elastic strand 28 to product portions of the elastic strand 28 with more volume than other portions which may only receive one of the first and second streams of adhesive (either one could be left on by keeping the associated valve open continuously). It will be understood that different operations with the nozzle 1210 are possible, including those set forth below.

In another example set forth in FIGS. 22A and 22B, one portion of the elastic strand 28 receives adhesive from only the second expansion chamber 1258 in FIG. 22A, e.g., by having the second valve 1114 in the module 1110 open flow of the second adhesive stream while the first valve 1112 closes flow of the first adhesive stream. Although the first adhesive passage 1240 is shown empty for the sake of illustration clarity in FIG. 22A, it will be understood that this would normally be filled with the first adhesive stream, but the adhesive would remain within the first adhesive passage 1240 based on the small sizing of the first nozzle outlet 1242.

FIG. 22B shows the elastic strand 28 after movement in the machine direction a small distance as shown by the arrows in these Figures, and in this state the first valve 1112 is opened to force the first adhesive stream into the first expansion chamber 1256 and onto the elastic strand 28 while the second valve 1114 has been closed, terminating flow of the second adhesive stream. As a result, this portion downstream from the previously-coated portion of the elastic strand 28 receives the first adhesive stream rather than the second adhesive stream, these different coatings being visible with different cross-hatching in FIG. 22B. When the first and second adhesive streams are set to provide different flow rates or volumes of adhesive material, the resulting coatings on the different portions of elastic strand 28 will have varying volumes of adhesive, which is advantageous for the reasons set forth above (including adhesive savings in a central portion of the elastic strand 28 following adherence to a substrate).

Additionally, the operation shown in FIGS. 22A and 22B also enables two different types of adhesive materials to be applied to the different portions of the elastic strand 28 in yet another embodiment. To this end, the first adhesive stream in such an embodiment would consist of a first type of adhesive material that is to be applied to the opposing ends or the first and third portions of elastic strands 28, while the second adhesive stream would consist of a second type of adhesive material that is to be applied to the central portion or second portion of elastic strands 28. The first and second types of adhesive material would be different from one another in this embodiment. For example, the first adhesive stream in one example is a stronger bonding adhesive such as elastic attachment adhesives, while the second adhesive stream is an inexpensive adhesive such as construction glue. The elastic attachment adhesives, which are available from many suppliers including National Adhesives of Bridgewater, N.J., are configured to limit movement of opposing ends of the elastic strand 28 to avoid creep after the hygiene product is assembled, and the construction glues, which are also available from many suppliers such as National Adhesives of Bridgewater, N.J., are configured to allow the elastic strands 28 at the central portion to retract from its stretched condition (provides elasticity to the hygiene products).

As the construction glue would be applied to a majority of the elastic strands 28, such an embodiment would provide significant cost savings over conventional designs that apply constant coatings of the stronger bonding elastic attachment adhesives to the entirety of elastic strands. Of course, in such embodiments the two types of adhesive must be capable of being applied at the same temperature so that the heater 1142 and any other temperature control devices in the module 1110 and nozzle 1210 could provide uniform heating to the adhesive to reach an elevated temperature within the standard operating application temperature ranges for both adhesive types (based on viscosity, primarily) prior to discharge onto the elastic strands 28. Regardless of the particular material(s) chosen, the operation of the module 1110 and nozzle 1210 of this embodiment provides significant add-on weight and cost savings for adhesive material in a hygiene product, while also avoiding any adverse effects on control responsiveness at the first and second valves 1112, 1114.

In these embodiments, the adhesive streams form a coating on the elastic strand 28 that appears continuous to the naked eye, but it is believed that this coating is not entirely continuous along the length of the elastic strand 28. As described above, the adhesive is extruded from the first and second nozzle outlets 1242, 1246 into the first and second expansion chambers 1256, 1258 and then onto the elastic strand 28. Consequently, the adhesive contacts the moving elastic strand 28 and rapidly accelerates, which causes the adhesive to be applied in a semi-starved state such that the amount of adhesive varies along the length of the elastic strand 28. More particularly, the adhesive is believed to form localized masses or thicker sections separated by thinner sections as the adhesive is accelerated. These localized masses of adhesive are configured to become discrete bond points when securing the elastic strand 28 to substrates. Then when the adhesive is struck with air from the air outlet 1270, it causes additional spreading of the adhesive that tends to further spread the adhesive into localized masses which are desirable as set forth above.

Figure 23:
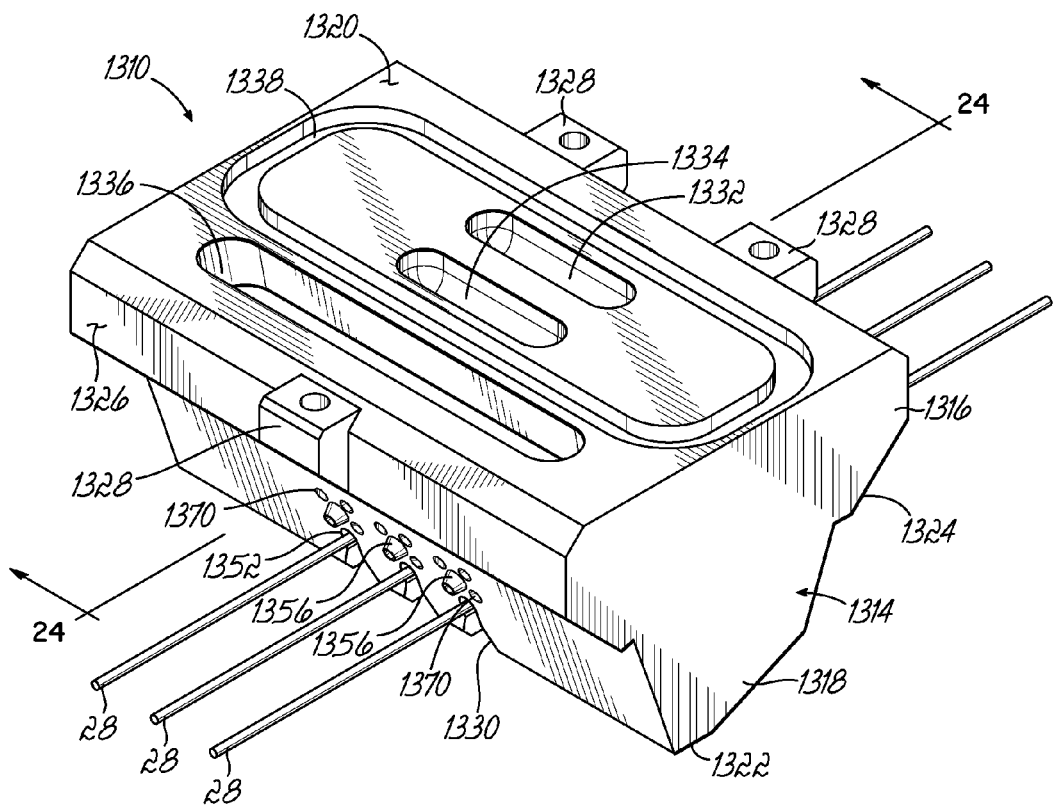
FIG. 23 is a top perspective view of one embodiment of a non-contact dispensing nozzle including separated nozzle inlets configured to be used with the module of FIG. 18 in another version of a dispensing apparatus.
Figure 24:
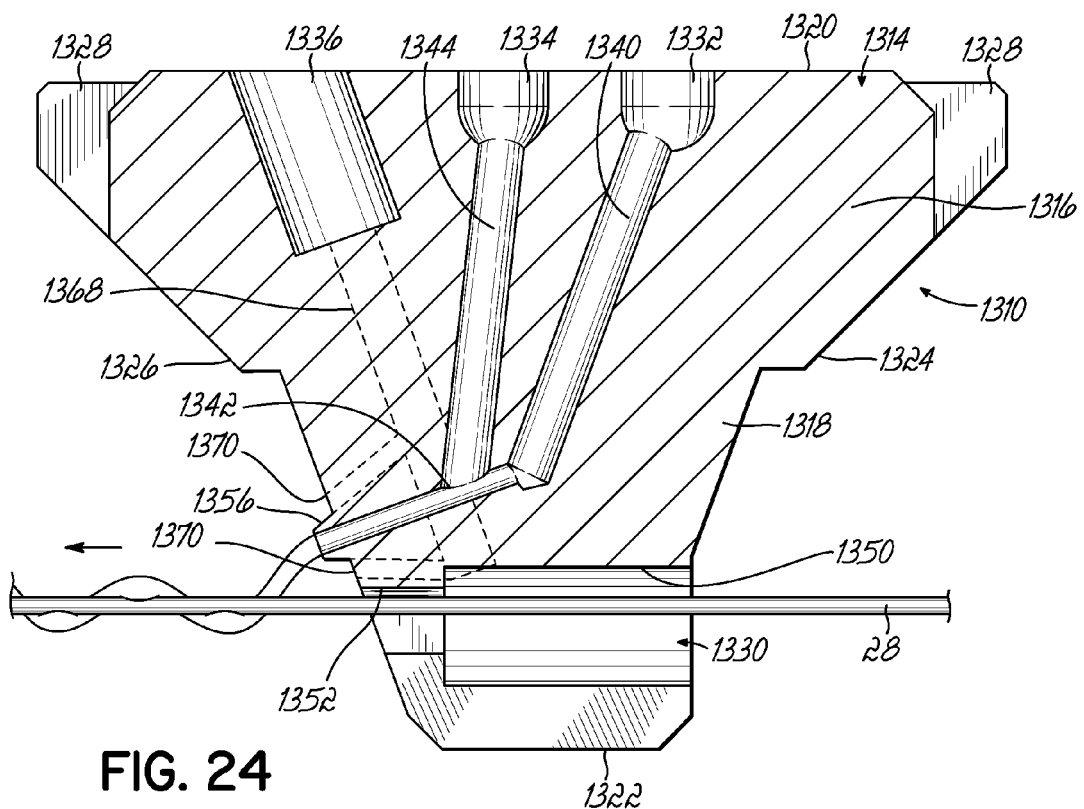
FIG. 24 is a cross-sectional side view of the dispensing nozzle of FIG. 23, taken along line 24-24 at the location of one of the elastic strands, showing further details of internal adhesive and air flow passages within the nozzle as well as a schematic illustration of an adhesive filament being applied to the moving elastic strand.

Another embodiment of a non-contact dispensing nozzle 1310 is illustrated in FIGS. 23 and 24 for use with the module 1110 having separated first and second module outlets 1126, 1136. The nozzle 1310 is a modified version of the SureWrap™ Elastic Attachment Nozzle commercially available from Nordson Corporation of Westlake, Ohio, several versions of which are described in U.S. Pat. No. 7,578,882 to Harris et al., initially referenced above. Although only one version of this modified embodiment of the nozzle 1310 is described in detail and shown in FIGS. 23 and 24, it will be understood that the additional features and modifications shown in other embodiments of the Harris '882 Patent and other subsequent related patent documents may also be included, if desired, without departing from the scope of this disclosure.

In FIGS. 23 and 24, similar elements of the nozzle 1310 which are not modified or largely identical to those elements of the previous embodiment at nozzle 1210 have been applied with similar reference numbers in the "1300" series without further explanation below where the changes are not pertinent to the current invention. These elements include the nozzle body 1314, the upper body portion 1316, the lower body portion 1318, the top side 1320, the bottom side 1322, the front side 1324, the rear side 1326, the connection portions 1328, the first nozzle inlet 1332, the second nozzle inlet 1334, the air inlet 1336, the seal groove 1338, the first adhesive passage 1340, the second adhesive passage 1344, and the air passage 1368. As with the previous embodiment, the nozzle 1310 selectively receives at the first nozzle inlet 1332 a first adhesive stream from the first module outlet 1126 when the first valve 1112 is opened, and selectively receives at the second nozzle inlet 1334 a second adhesive stream from the second module outlet 1136 when the second valve 1114 is opened. The air inlet 1336 receives pressurized air which may also be delivered through the module 1110, although it could be delivered through other known devices as well into the nozzle 1310. Unlike the previous embodiment of nozzle 1210, this dispensing nozzle 1310 applies a filament of adhesive in a non-contact dispensing onto the elastic strand(s) 28.

To this end, in this embodiment the bottom side 1322 of the nozzle 1310 includes a slot 1330 in the form of a V-shaped notch defined by two converging surfaces. The slot 1330 of this embodiment includes a larger upstream portion 1350 intersecting the front side 1324 and a smaller downstream portion 1352 intersecting the rear side 1326. The larger upstream portion 1350 ensures that no sharp edges are run into the elastic strands 28 as the elastic strands 28 enter the nozzle 1310. It will be understood that a strand guide element may be positioned within this upstream portion 1350 of the slot 1330 in some embodiments (not shown). Alternatively, what is shown in FIGS. 23 and 24 is that the smaller downstream portion 1352 of slot 1330 defines a strand guide portion for the nozzle 1310, effectively by positioning the elastic strand 28 accurately under the corresponding air and adhesive outlets described further below. As with the previous embodiment, the specific shape and configuration of the slot 1330 may be modified in other embodiments without departing from the scope of this disclosure, so long as the elastic strand(s) 28 are accurately positioned to receive filaments of adhesive.

With specific reference to FIG. 24, the second adhesive passage 1344 of this nozzle 1310 intersects the first adhesive passage 1340 at a juncture 1342 within the interior of the nozzle body 1314. The first and second adhesive passages 1340, 1344 then share a combined flow path to a single nozzle outlet 1356. To this end, the nozzle 1310 of this embodiment consists of only a single nozzle outlet 1356 for each pair of first and second adhesive passages 1340, 1344 (once again, there may be multiple pairs of parallel first and second adhesive passages 1340, 1344 in communication with the first and second nozzle inlets 1332, 1334 as set forth above, for coating different elastic strands 28 with the nozzle 1310. This single nozzle outlet 1356 projects slightly outwardly from the rear side 1326 at a location directly above and in line with the elastic strand 28 moving through the slot 1330. Consequently, the single nozzle outlet 1356 is configured to discharge a filament of adhesive when one or both of the first and second valves 1112, 1114 of the module 1110 are opened to apply varying volumes of adhesive onto the elastic strand 28 using the first and/or second adhesive streams.

The air passage 1368 of this embodiment of the nozzle 1310 splits apart within the interior of the nozzle body 1314 and terminates at a series of air outlets 1370 in the rear side 1326. The air outlets 1370 in this embodiment include four air outlets 1370 per nozzle outlet 1356, with the four air outlets 1370 arranged so as to surround the nozzle outlet 1356. However, as identified by alternative embodiments in the Harris '882 Patent, these air outlets 1370 and the number thereof could be modified depending on the needs of the end user (e.g., the need for a specific swirling pattern for the adhesive filament). The divided portion of the air passage 1368 leading to the air outlets 1370 is shown in phantom in FIG. 24 because these elements move out of plane with the adhesive passages 1340, 1344 so as to avoid intersection and interference of air flow with adhesive stream flows. Likewise, it will be understood that the particular compound angling of the axes of the air outlets 1370 relative to the axis of the nozzle outlet 1356 may be modified without departing from the scope of this disclosure. Pressurized air streams are discharged from the set of air outlets 1370 so as to move towards a periphery of the filament of adhesive being discharged from the nozzle outlet 1356 (e.g., the air streams are directed generally tangential to the adhesive filament), and these pressurized air streams typically impart rotation and/or swirling movement of the filament as it flies towards the elastic strand 28. Such rotation and/or swirling movement leads to a wrapping of the adhesive around the elastic strand 28 as schematically shown in FIG. 24, and this provides discrete bond points as desired for all the reasons set forth above. After the filament of adhesive has been deposited on the elastic strand 28, portions of the filament may also be drawn by gravity and/or centrifugal forces to further wrap around the elastic strand 28 to form the coating defining discrete bond points.

The operation of the nozzle 1310 and module 1110 may be summarized as follows. The elastic strand 28 is guided by the slot 1330 to move underneath the single nozzle outlet 1356 projecting from the rear side 1326. One of the first and second valves 1112, 1114 at the module 1110 is opened to cause discharge of a filament of adhesive towards first and third portions of the elastic strand 28, while the other of the first and second valves 1112, 1114 is opened to cause discharge of a filament of adhesive towards the second portion of the elastic strand 28. The first and second adhesive streams are provided in this embodiment with different pressures and/or flow rates such that the first and third portions of the elastic strand 28 are coated with a volume (per unit length) of adhesive that is larger than the volume of adhesive coated on the second portion of the elastic strand 28. Because the adhesive filament dispensed varies in volume/flow rate, it will be understood that a control may also be adjusting the air flow rate delivered through the air passage 1368 and the set of air outlets 1370 to ensure proper swirling motion of the filament regardless of the adhesive volume changes. For example, a higher flow of pressurized air may be discharged to move the adhesive filament when the larger of the first and second adhesive streams is discharged at the nozzle outlet 1356.

It will be understood that the operation of the nozzle 1310 may be modified in other embodiments. For example, instead of having the first and second valves 1112, 1114 alternate with one open and one closed at all times, both valves 1112, 1114 could be opened when the larger volume of adhesive is to be dispensed onto the elastic strand 28 (and then only one of the first and second valves 1112, 1114 would remain open to discharge the filament on the second portion or central portion of the elastic strand 28). The adhesive streams would combine when the first and second valves 1112, 1114 are open at the juncture 1342 within the nozzle body 1314, but this juncture 1342 is still sufficiently far removed enough from the first and second valves 1112, 1114 that any difference in pressures between the two adhesive streams do not adversely affect the controlled opening and closing of the valves 1112, 1114 (which must be precise in order to coat rapidly-moving elastic strands 28 with the proper volumes of adhesive in each portion). Thus, this embodiment of the nozzle 1310 enables the same benefits as the previous embodiments described above, particularly in a non-contact dispensing setting, when that is desired by the end user.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the general inventive concept.

What is claimed is:

1. A method of dispensing adhesive onto a stretched elastic strand during the manufacturing of personal disposable hygiene products, the method comprising:
    moving the stretched elastic strand in a machine direction;
    delivering a first adhesive stream from a first adhesive supply and a second adhesive stream from a second adhesive supply through a module and into a dispensing nozzle, the first and second adhesive streams remaining separate during movement through the module and into the nozzle;

controlling flow of the first and second adhesive streams to cause dispensing of adhesive at the nozzle, the dispensing further including:
applying a first volume of adhesive onto a first portion of the elastic strand;
applying a second volume of adhesive onto a second portion of the elastic strand located downstream from the first portion of the elastic strand relative to the machine direction;
applying a third volume of adhesive onto a third portion of the elastic strand located downstream from the second portion of the elastic strand relative to the machine direction, wherein the second volume of adhesive is less than each of the first volume of adhesive and less than the third volume of adhesive;
contacting the stretched elastic strand with first and second substrate layers to adhesively secure the elastic strand with the volumes of adhesive between the first and second substrate layers and to form a bond therebetween; and
releasing the stretched elastic strand to allow the elastic strand to retract from its stretched condition, thereby collectively defining an elasticized portion of the hygiene product with the first and second substrate layers,
the first and third portions of the elastic strand defining opposing ends of the elastic strand, and the second portion of the elastic strand defining a central portion of the elastic strand extending between the opposing ends, when the elastic strand is secured between the first and second substrate layers, and
the first and third volumes of adhesive limiting movement of the opposing ends of the elastic strand relative to the first and second substrate layers while maintaining the bond, and the second volume of adhesive being sufficiently low to allow the elastic strand to retract from its stretched condition.

2. The method of claim 1, wherein the nozzle includes a first nozzle outlet and a second nozzle outlet, and the method further comprises:
maintaining separation between the first and second adhesive streams during flow through the nozzle, such that the first adhesive stream is selectively discharged at the first nozzle outlet and the second adhesive stream is selectively discharged at the second nozzle outlet to thereby dispense adhesive onto the stretched elastic strand.

3. The method of claim 2, wherein the first nozzle outlet includes a first expansion chamber communicating with a strand guide portion of the nozzle, the second nozzle outlet includes a second expansion chamber communicating with the strand guide portion, and moving the elastic strand further comprises:
guiding the elastic strand with the strand guide portion to move underneath the first expansion chamber and the second expansion chamber in sequence during movement along the machine direction.

4. The method of claim 3, wherein dispensing of adhesive at the nozzle further comprises:
contacting the first adhesive stream with the elastic strand at the first expansion chamber to contact dispense adhesive onto the elastic strand when the first adhesive stream is controlled to flow through the nozzle; and
contacting the second adhesive stream with the elastic strand at the second expansion chamber to contact dispense adhesive onto the elastic strand when the second adhesive stream is controlled to flow through the nozzle.

5. The method of claim 4, wherein controlling flow of the first and second adhesive streams into the nozzle further comprises:
opening flow of the first and second adhesive streams into the nozzle at the same time to thereby apply adhesive onto the elastic strand at the first expansion chamber and then apply additional adhesive onto the elastic strand at the second expansion chamber, to provide a wet-on-wet contact dispensing of both the first and second adhesive streams onto portions of the elastic strand.

6. The method of claim 3, wherein the strand guide portion includes a first groove extending between the first and second expansion chambers and a second groove extending downstream from the second expansion chamber, and moving the elastic strand further comprises:
moving the elastic strand through the first groove as the elastic strand moves in the machine direction between the first and second expansion chambers; and
moving the elastic strand through the second groove as the elastic strand moves in the machine direction away from the second expansion chamber,
the second groove being larger in size than the first groove such that a larger volume of adhesive can be carried by the elastic strand during movement away from the second expansion chamber compared to during movement of the elastic strand between the first and second expansion chambers.

7. The method of claim 3, wherein the nozzle includes an air outlet positioned along a rear side of the nozzle, and the method further comprises:
guiding the elastic strand to move underneath the air outlet after moving underneath the first and second expansion chambers during movement along the machine direction; and
discharging pressurized air from the air outlet towards adhesive in contact with the elastic strand as the elastic strand moves past the rear side of the nozzle, the pressurized air assisting with spreading of the adhesive around the elastic strand.

8. The method of claim 1, wherein the nozzle includes a single nozzle outlet, and the method further comprises:
combining the first and second adhesive streams during flow through the nozzle, such that each of the first and second adhesive streams is selectively discharged at the single nozzle outlet to thereby dispense adhesive onto the stretched elastic strand.

9. The method of claim 8, wherein the nozzle includes a strand guide portion, and the method further comprises:
guiding the elastic strand with the strand guide portion to move underneath the single nozzle outlet during movement along the machine direction; and
discharging at least one of the first and second adhesive streams from the single nozzle outlet as a filament that travels towards the elastic strand, thereby non-contact dispensing adhesive onto the elastic strand when at least one of the first and second adhesive streams is controlled to flow through the nozzle.

10. The method of claim 9, wherein the nozzle includes a plurality of air outlets proximate to the single nozzle outlet, and dispensing of adhesive at the nozzle further comprises:
discharging air streams from the plurality of air outlets to generate swirling motion in the filament as the filament travels towards the elastic strand; and adjusting a volume of air discharged in the air streams based on changes in adhesive volume being discharged through the single nozzle outlet as a result of controlling flow of the first and second adhesive streams into the nozzle.

11. The method of claim 1, wherein the module includes a first valve and a second valve, and controlling flow of the first and second adhesive streams into the nozzle further comprises:
opening and closing the first valve to selectively enable flow of the first adhesive stream through the module and into the nozzle; and
opening and closing the second valve to selectively enable flow of the second adhesive stream through the module and into the nozzle.

12. The method of claim 11, wherein applying the first, second, and third volumes of adhesive onto the elastic strand further comprises:
opening the first valve while leaving the second valve closed to apply the first volume of adhesive onto the first portion of the elastic strand;
closing the first valve to stop applying the first volume of adhesive;
opening the second valve while leaving the first valve closed to apply the second volume of adhesive onto the second portion of the elastic strand;
closing the second valve to stop applying the second volume of adhesive; and
opening the first valve while leaving the second valve closed to apply the third volume of adhesive onto the third portion of the elastic strand.

13. The method of claim 11, wherein applying the first, second, and third volumes of adhesive onto the elastic strand further comprises:
opening the first and second valves to apply the first volume of adhesive to the first portion of the elastic strand;
closing the second valve while leaving the first valve open to apply the second volume of adhesive to the second portion of the elastic strand; and
opening the first and second valves to apply the third volume of adhesive to the third portion of the elastic strand.

14. The method of claim 1, wherein delivering the first and second adhesive streams through the module further comprises:
delivering a first type of adhesive material from the first adhesive supply to form the first adhesive stream; and
delivering a second type of adhesive material, which is different than the first type of adhesive material, from the second adhesive supply to form the second adhesive stream.

15. The method of claim 14, wherein the first type of adhesive material defines the first and third volumes of adhesive, the second type of adhesive material defines the second volume of adhesive, and the first type of adhesive material is a stronger bonding adhesive than the second type of adhesive material.

16. A method of dispensing adhesive onto a stretched elastic strand during the manufacturing of personal disposable hygiene products, the method comprising:
moving the stretched elastic strand in a machine direction;
delivering a first adhesive stream consisting of a first type of adhesive material from a first adhesive supply and a second adhesive stream consisting of a second type of adhesive material from a second adhesive supply through a module and into a dispensing nozzle, the first and second adhesive streams remaining separate during movement through the module and into the nozzle, and the first and second types of adhesive material being different from one another;
controlling flow of the first and second adhesive streams to cause dispensing of adhesive at the nozzle, the dispensing further including:
applying the first adhesive stream onto a first portion of the elastic strand;
applying the second adhesive stream onto a second portion of the elastic strand located downstream from the first portion of the elastic strand relative to the machine direction;
applying the first adhesive stream onto a third portion of the elastic strand located downstream from the second portion of the elastic strand relative to the machine direction;
contacting the stretched elastic strand with first and second substrate layers to adhesively secure the elastic strand with the adhesive between the first and second substrate layers and to form a bond therebetween; and
releasing the stretched elastic strand to allow the elastic strand to retract from its stretched condition, thereby collectively defining an elasticized portion of the hygiene product with the first and second substrate layers,
the first and third portions of the elastic strand defining opposing ends of the elastic strand, and the second portion of the elastic strand defining a central portion of the elastic strand extending between the opposing ends, when the elastic strand is secured between the first and second substrate layers, and
the first type of adhesive material limiting movement of the opposing ends of the elastic strand relative to the first and second substrate layers while maintaining the bond, and the second type of adhesive material being configured to allow the elastic strand to retract from its stretched condition.

17. The method of claim 16, wherein the first type of adhesive material is a stronger bonding adhesive than the second type of adhesive material.

18. The method of claim 17, wherein the first type of adhesive material is an elastic attachment adhesive, and the second type of adhesive material is a construction glue.

19. The method of claim 17, further comprising:
heating the first and second adhesive streams to an elevated temperature with a heater associated with the module, the elevated temperature being within standard operating application temperature ranges for both of the first and second types of adhesive material.

20. The method of claim 17, wherein the first and third portions of the elastic strand collectively define a first length and the second portion of the elastic strand defines a second length larger than the first length, and controlling flow of the first and second adhesive streams further comprises:
applying the second adhesive stream onto a majority of the elastic strand.

21. The method of claim 17, wherein the module includes a first valve and a second valve, and applying the first and second adhesive streams onto the elastic strand further comprises:
opening the first valve while leaving the second valve closed to apply the first adhesive stream onto the first portion of the elastic strand;
closing the first valve to stop applying the first adhesive stream;

opening the second valve while leaving the first valve closed to apply the second adhesive stream onto the second portion of the elastic strand;

closing the second valve to stop applying the second adhesive stream; and opening the first valve while leaving the second valve closed to apply the first adhesive stream onto the third portion of the elastic strand.

22. The method of claim 16, wherein the nozzle includes a first nozzle outlet and a second nozzle outlet, and the method further comprises:

maintaining separation between the first and second adhesive streams during flow through the nozzle, such that the first adhesive stream is selectively discharged at the first nozzle outlet and the second adhesive stream is selectively discharged at the second nozzle outlet.

* * * * *